US009662219B2

(12) United States Patent
Bonin, Jr. et al.

(10) Patent No.: US 9,662,219 B2
(45) Date of Patent: May 30, 2017

(54) ORTHOPEDIC PROSTHESIS WITH SUTURE ANCHOR FEATURES

(71) Applicant: Smith & Nephew, Inc., Memphis, TN (US)

(72) Inventors: Henry K. Bonin, Jr., Denver, CO (US); Joseph M. Ferrante, Bartlett, TN (US); Matthew E. Koski, Westford, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/412,536

(22) PCT Filed: Jul. 2, 2013

(86) PCT No.: PCT/US2013/049019
§ 371 (c)(1),
(2) Date: Jan. 2, 2015

(87) PCT Pub. No.: WO2014/008229
PCT Pub. Date: Jan. 9, 2014

(65) Prior Publication Data
US 2015/0190237 A1 Jul. 9, 2015

Related U.S. Application Data

(60) Provisional application No. 61/667,621, filed on Jul. 3, 2012.

(51) Int. Cl.
A61F 2/40 (2006.01)
A61B 17/04 (2006.01)
(Continued)

(52) U.S. Cl.
CPC ............ A61F 2/40 (2013.01); A61B 17/0401 (2013.01); A61B 17/8061 (2013.01); A61B 17/82 (2013.01);
(Continued)

(58) Field of Classification Search
CPC ........ A61F 2/40; A61F 2/4014; A61F 2/4059; A61F 2002/4011;
(Continued)

(56) References Cited

U.S. PATENT DOCUMENTS 5,376,126 A 12/1994 Lin
2005/0107797 A1* 5/2005 Romeo .............. A61B 17/0483
606/74

(Continued)

FOREIGN PATENT DOCUMENTS

CN 101272743 A 9/2008
CN 102159142 A 8/2011
(Continued)

OTHER PUBLICATIONS

Chinese Patent Office, First Office Action, dated Dec. 1, 2015, 15 pages, including English Translation.
(Continued)

Primary Examiner — Christian Sevilla
Assistant Examiner — Megan Wolf
(74) Attorney, Agent, or Firm — Taft Stettinius & Hollister LLP

(57) ABSTRACT

An orthopedic prosthesis (20, 100) including an implant body (22, 24, 26, 122) defining a number of suture anchor attachment locations (30, 120), and a plurality of suture anchors (40) each including one or more suture (S) extending from an anchor portion (42) that is engaged with a select one of the suture anchor attachment locations (30, 120) to selectively attach a corresponding one of the suture anchors (40) to the implant body (22, 24, 26, 122). A method of using the orthopedic prosthesis (20, 100) is also provided.

24 Claims, 9 Drawing Sheets

(51) Int. Cl.
*A61B 17/80* (2006.01)
*A61B 17/82* (2006.01)
*A61F 2/30* (2006.01)

(52) U.S. Cl.
CPC ............ *A61F 2002/30331* (2013.01); *A61F 2002/30405* (2013.01); *A61F 2002/30461* (2013.01); *F04C 2270/0421* (2013.01)

(58) Field of Classification Search
CPC ............ A61F 2002/4018–2002/4055; A61F 2002/4062–2002/4077
See application file for complete search history.

(56) References Cited

U.S. PATENT DOCUMENTS

| | | |
|---|---|---|
| 2005/0267476 A1 | 12/2005 | Chervitz et al. |
| 2007/0191957 A1 | 8/2007 | Anderson et al. |
| 2008/0004702 A1 | 1/2008 | Denoziere |
| 2008/0125780 A1 | 5/2008 | Ferree |
| 2008/0228281 A1* | 9/2008 | Forrer .................. A61F 2/4014 623/19.12 |
| 2009/0287215 A1 | 11/2009 | Fisher et al. |
| 2011/0224799 A1 | 9/2011 | Stone |
| 2012/0035733 A1* | 2/2012 | Porter .................. A61F 2/0811 623/18.11 |
| 2013/0172944 A1* | 7/2013 | Fritzinger .......... A61B 17/0401 606/286 |
| 2014/0114425 A1* | 4/2014 | Ekelund ............. A61F 2/30728 623/19.14 |

FOREIGN PATENT DOCUMENTS

| | | |
|---|---|---|
| EP | 2455002 A1 | 5/2012 |
| WO | 9641574 A2 | 12/1996 |
| WO | 0057820 A1 | 10/2000 |
| WO | 2008034276 A2 | 3/2008 |
| WO | 2009128846 A1 | 10/2009 |
| WO | 2011040917 A1 | 4/2011 |
| WO | WO 2011040917 A1 * | 4/2011 ......... A61B 17/0401 |

OTHER PUBLICATIONS

European Patent Office, European Search Report, dated Apr. 5, 2016, 8 pages.
Chinese Search Report; State Intellectual Property Office of People's Republic of China; Chinese Patent Application No. 201380046004.7; Sep. 13, 2016; 5 pages.
Chinese Office Action; State Intellectual Property Office of People's Republic of China; Chinese Patent Application No. 201380046004.7; Sep. 28, 2016; 12 pages.
European Examination Report; European Patent Office; European Application No. 13812956.4; Oct. 24, 2016; 18 pages.

* cited by examiner

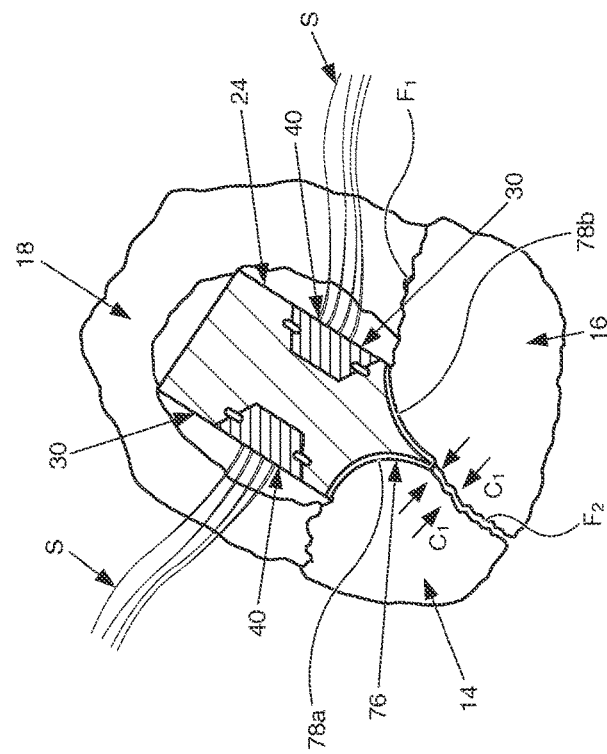
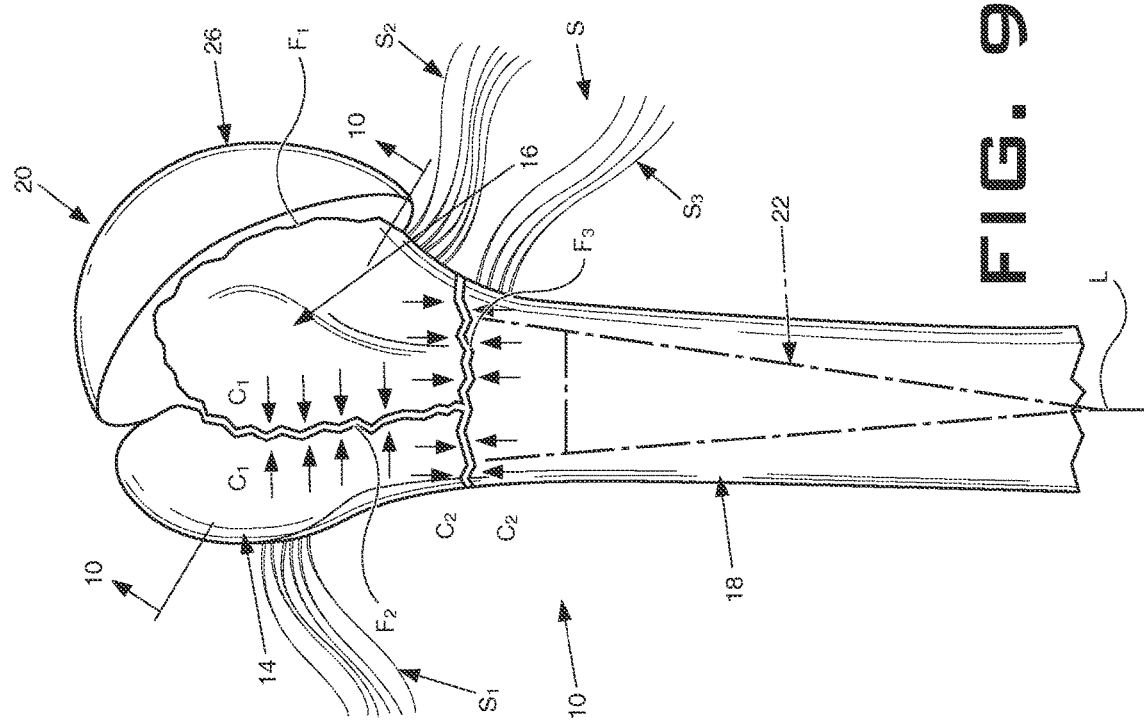

ORTHOPEDIC PROSTHESIS WITH SUTURE ANCHOR FEATURES

CROSS REFERENCE TO RELATED APPLICATIONS

This application is a United States National Phase filing of International Application No. PCT/US2013/043559, filed Jul. 2, 2013, which claims priority to and the benefit of U.S. Provisional Patent Application No. 61/667,621 filed on Jul. 3, 2012, the contents of which are incorporated herein by reference in their entirety.

FIELD OF THE INVENTION

The present invention relates generally to orthopedic prostheses, and more particularly but not exclusively relates to an orthopedic prosthesis including suture anchor features configured to selectively attach sutures to one or more regions of the prosthesis.

BACKGROUND

Referring to FIG. 1, shown therein is the upper extremity of the humerus 10 which generally includes a humeral head 12, a greater tuberosity 14, a lesser tuberosity 16, and a humeral shaft 18. Referring to FIG. 2, in a traumatic accident or other traumatic events, the upper extremity of the humerus 10 may break into several fragments along multiple fracture lines, with the humeral head 12 separating along a fracture line $F_1$ at or near the anatomical neck, the greater tuberosity 14 separating from the lesser tuberosity 16 along a fracture line $F_2$ at or near the biciptal groove, and/or the humeral shaft 18 separating along a fracture line $F_3$ at or near the surgical neck. The resulting fracture is generally referred to as a "four-part humeral fracture". Attached to the displaced tuberosity fragments are muscles and tendons of the rotator cuff (not shown), namely the subscapularius, supraspinatous, infraspinatous, and teres minor.

When the humeral head fragment is significantly displaced or damaged, the surgeon may choose to repair this type of fracture by replacing the anatomical humeral head 12 with a hemispherical prosthesis head attached to a prosthesis stem which is in turn anchored within the humeral shaft 18. The remaining fragments, namely the greater and lesser tuberosity fragments 14, 16, are reduced about the prosthesis body and under the hemispherical prosthesis head. The greater and lesser tuberosity fragments 14, 16 are typically held in place via sutures. Conventional shoulder prostheses may be provided with suture openings for threading sutures therethrough to tie the tuberosity fragments 14, 16 to the humeral shaft 18 and/or to one another. Alternatively, the sutures can be attached directly to the tuberosity fragments 14, 16 and/or to the humeral shaft 18. However, current methods for attaching sutures to prosthetic devices and/or bone fragments can be tedious and time-consuming, and generally add to the overall length and complexity of the surgical procedure.

Thus, there remains a need to provide an improved orthopedic prosthesis including suture anchor features configured to selectively attach sutures to one or more regions of the prosthesis. The present invention satisfies this need and provides other benefits and advantages in a novel and unobvious manner.

SUMMARY

While the actual nature of the invention covered herein can only be determined with reference to the claims, certain forms of the invention that are characteristic of the embodiments disclosed herein are described briefly as follows.

In general, an orthopedic prosthesis is provided which includes suture anchor features configured to selectively attach sutures to one or more regions of the prosthesis. In one embodiment, the orthopedic prosthesis may be provided as a modular implant including a stem configured for anchoring within a bone, a prosthetic head coupled to the stem, and a number of suture anchor features configured to selectively attach sutures to one or more regions of the stem or prosthetic head. In another embodiment, the orthopedic prosthesis may be provided as a plate configured for anchoring to bone via a number of anchors or fasteners, and including a number of suture anchor features configured to selectively attach sutures to one or more regions of the plate.

It is one object of the present invention to provide an improved orthopedic prosthesis. Further embodiments, forms, features, aspects, benefits, objects, and advantages of the present invention will become apparent from the detailed description and figures provided herewith.

BRIEF DESCRIPTION OF THE DRAWINGS

FIG. 9 is a side perspective view of the upper extremity of a fractured humerus with the orthopedic prosthesis of FIG. 3 attached thereto.

FIG. 10 is a partial cross-sectional view of the upper extremity of the fractured humerus with the orthopedic prosthesis of FIG. 3 attached thereto, as taken along line 10-10 of FIG. 9.

DESCRIPTION OF THE ILLUSTRATED EMBODIMENTS

Figure 2:
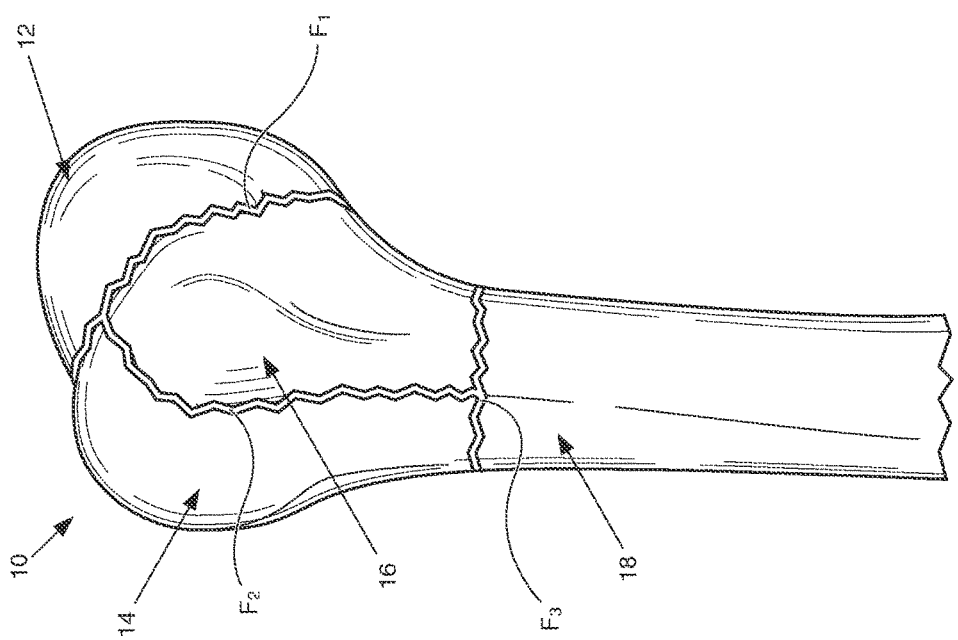
FIG. 2 is a perspective view of the upper extremity of a fractured humerus.
Figure 1:
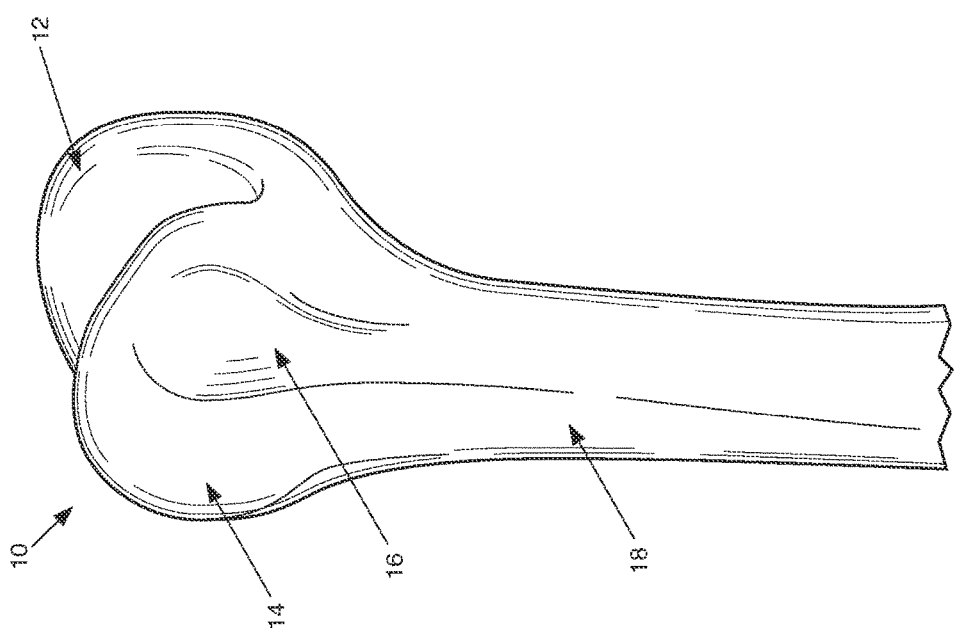
FIG. 1 is a perspective view of the upper extremity of the humerus.

For the purpose of promoting an understanding of the principles of the present invention, reference will now be made to the embodiments illustrated in the drawings and specific language will be used to describe the same. It will nevertheless be understood that no limitation of the scope of the invention is hereby intended. Any alterations and further modifications in the described embodiments, and any further applications of the principles of the invention as described herein are contemplated as would normally occur to one skilled in the art to which the invention relates.

The following descriptions and illustrations of non-limiting embodiments of the present invention are exemplary in nature, it being understood that the descriptions and illustrations related thereto are in no way intended to limit the inventions disclosed herein and/or their applications and uses. Certain features and details associated with other embodiments of prosthetic devices and methods that may be used in association with the present invention are found in commonly owned U.S. Pat. No. 7,758,650 issued on Jul. 20, 2010 and U.S. Pat. No. 6,749,637 issued on Jun. 15, 2004, the contents of each patent incorporated herein by reference in their entirety.

Figure 3:
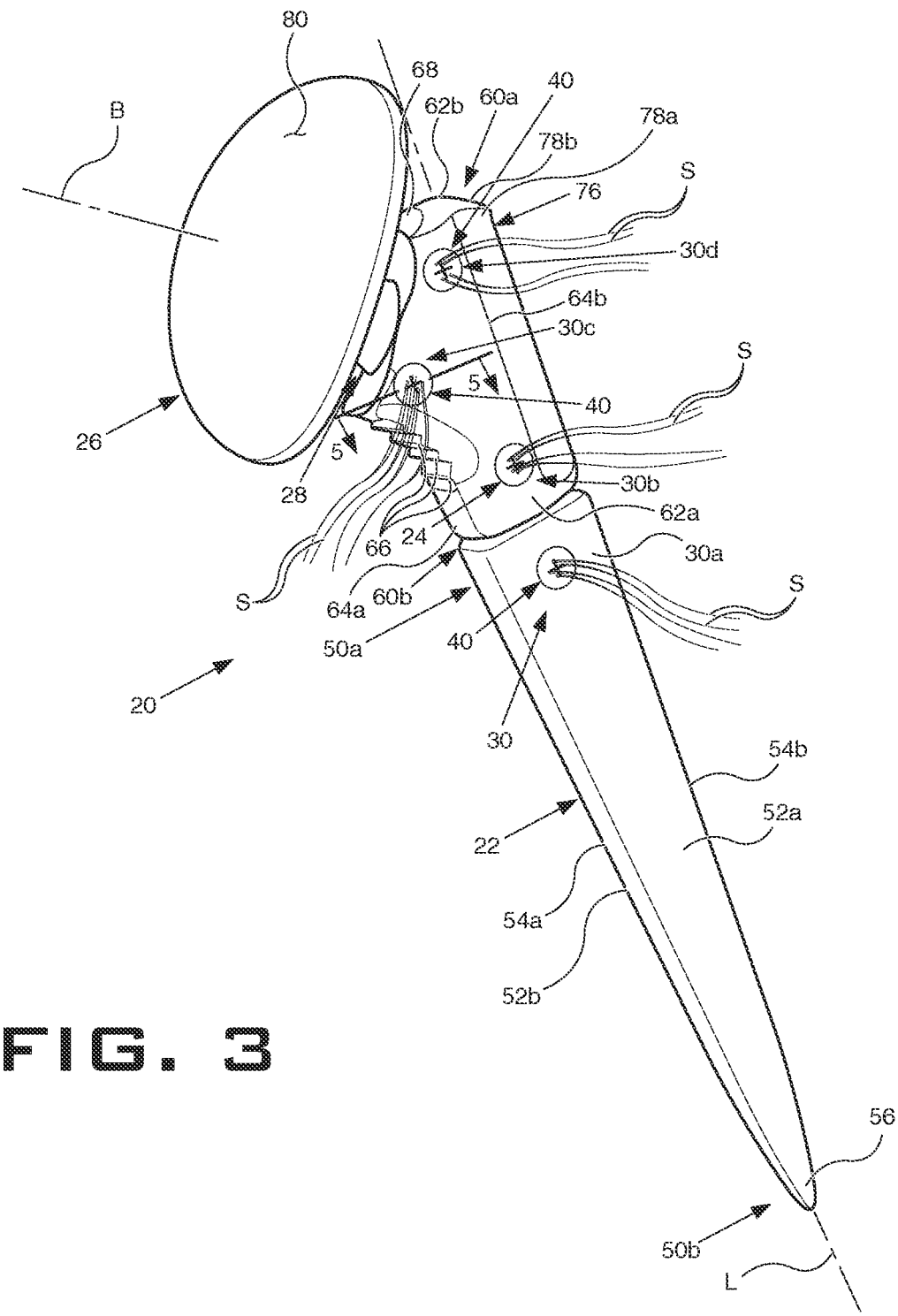
FIG. 3 is a perspective view of an orthopedic prosthesis according to one form of the present invention.
Figure 4:
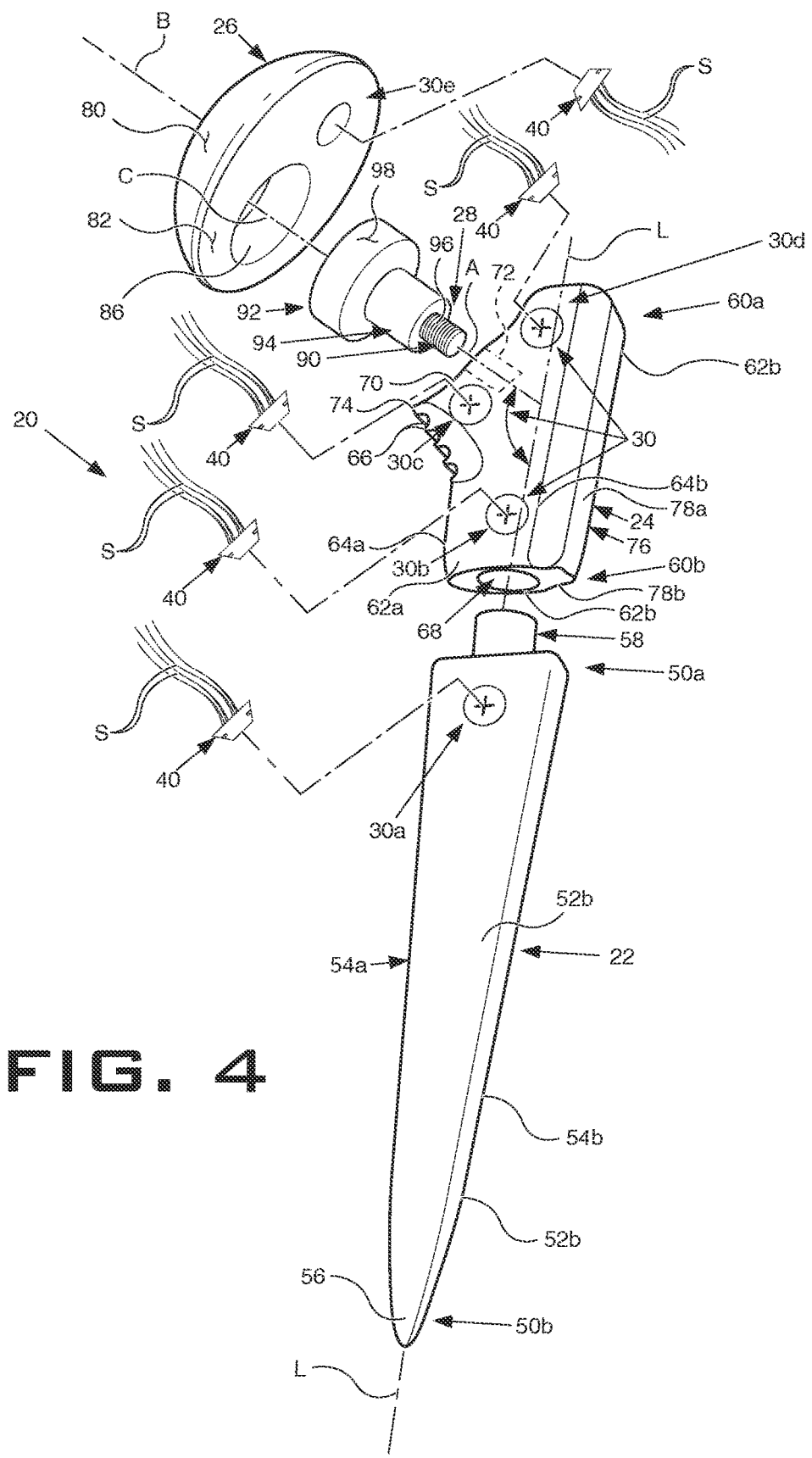
FIG. 4 is an exploded view of the orthopedic prosthesis of FIG. 3.

Referring to FIGS. 3 and 4, shown therein is an orthopedic prosthesis 20 according to one form of the present invention that, in the illustrated embodiment, is configured as a shoulder prosthesis for use in association with repair of one or more fractures of the upper extremity of the humerus 10 (FIG. 2). However, it should be understood that the orthopedic prosthesis 20 may be used in association with the repair of other bones and joints such as, for example, the hip and knee, and/or in association with other orthopedic surgeries or procedures.

In the illustrated embodiment, the prosthesis 20 generally includes a stem portion 22, a body portion 24 and a head portion 26, with the head portion 26 connected to the body portion 24 via an intermediate connector portion 28. The stem portion 22, the body portion 24 and/or the head portion 26 include a number of suture anchor attachment locations 30 configured for selective engagement with suture anchors 40, with each suture anchor 40 including one or more sutures S extending therefrom to thereby selectively attach the sutures S to the prosthesis 20. The various portions of the prosthesis 20 may be formed of metallic materials (i.e., stainless steel, titanium, metal alloys), polymeric materials (i.e., PEEK or other high strength polymers, copolymers or plastic materials), and/or other suitable materials known to those having ordinary skill in the art. Additionally, the suture anchors 40 may likewise be formed of metallic, polymeric, and/or other suitable materials which may be the same as or different from the material from which other portions of the prosthesis 20 are formed. The sutures S may be formed of synthetic materials including various polymers, biological materials, and/or other suitable suture materials known to those having ordinary skill in the art. Additionally, the sutures S may be formed of absorbable or non-absorbable materials. Further details regarding the attachment locations 30, the suture anchors 40, and the sutures S will be discussed in greater detail below.

In the illustrated embodiment, the stem 22 extends generally along a longitudinal axis L and includes a proximal end portion 50a and a distal end portion 50b. The stem 22 also has a generally rectangular cross section along the longitudinal axis L defined by a first pair of generally planar opposite side walls 52a, 52b that inwardly taper toward one another along the longitudinal axis L from the proximal end portion 50a to the distal end portion 50b, and a second pair of generally planar opposite side walls 54a, 54b that likewise inwardly taper toward one another along the longitudinal axis L from the proximal end portion 50a to the distal end portion 50b. The side walls 52a, 52b and 54a, 54b may be roughened to facilitate secure engagement with inner surfaces of the humeral shaft 18. Additionally, the distal end portion 50b may be provided with a pointed tip 56 to facilitate insertion into the humeral shaft 18. In the illustrated embodiment, the stem 22 has a tapered configuration for use in association with cementless prosthesis applications (i.e., secure engagement within an axial canal in bone without the use of cement). However, other embodiments are also contemplated where the stem 22 may be provided with a cylindrical configuration, or other shapes and configurations, for use in association with cemented prosthesis applications. In one embodiment, the proximal end portion 50a is provided with a generally cylindrical tapered shaft member 58 (FIG. 4) sized for receipt within a corresponding opening 68 (FIG. 4) in the body 24 to interconnect the stem 22 with the body 24. However, in other embodiments, the stem 22 and the body 24 may be provided as a unitary, single-piece structure. Additionally, in the illustrated embodiment, the stem 22 includes a pair of suture anchor attachment locations 30a arranged generally opposite one another along the opposite side walls 52a, 52b adjacent the proximal end portion 50a. However, it should be understood that the stem 22 may define any number of suture anchor attachment locations along other portions of the stem 22 including, for example, along the side walls 54a, 54b, along the distal end portion 50b, and/or along other portions of the stem 22. In other embodiments, the stem 22 need not include any or the suture anchor attachment locations 30. Although a particular configuration of the stem 22 has been illustrated and described herein, it should be understood that other types and configurations of the stem 22 are also contemplated.

In the illustrated embodiment, the body 24 extends generally along the longitudinal axis L and includes a proximal end portion 60a and a distal end portion 60b. The body 24 further includes a first pair of generally planar opposite side walls 62a, 62b that are generally aligned with the sides walls 52a, 52b of the stem 22, and a second pair of generally planar opposite side walls 64a, 64b that are generally aligned with the side walls 54a, 54b of the stem 22. At least a portion of the side wall 64a may be provided with a number of projections/grooves that together define a number of engagement structures or teeth 66 for receipt of one or more sutures to facilitate engagement or wrapping of sutures about the body 24, to facilitate bone in-growth into the body 24, to engage bone, and/or to offer additional support to the body 24. The distal end portion 60b includes a generally circular opening 68 (FIG. 4) sized for receipt of the tapered shaft member 58 (FIG. 4) of the stem 22 therein to interconnect the stem 22 with the body 24. In one embodiment, the opening 68 extends through the body 24 from the proximal end portion 60a to the distal end portion 60b generally along the longitudinal axis L, and the body 24 is further secured to the stem 22 by one or more pins or fasteners such as, for example, a screw or fastener (not shown) extending through the body 24 and threadingly engaged within a threaded aperture (not shown) in the tapered shaft member 58. However, it should be understood that the body 24 may be secured to the stem 22 via other structures or connection mechanisms. As discussed above, the stem 22 and the body 24 may alternatively be provided as a unitary, single-piece structure.

As shown in FIG. 4, the proximal end portion 60a of the body 24 includes a proximal end wall 70 that is inclined relative to the longitudinal axis L, and further includes an opening 72 extending through the proximal end wall 70 and into the body 24. The opening 72 is arranged generally along an inclined axis A that is angled relative to the longitudinal axis L at an inclination angle α. The opening 72 is sized for receipt of a first end portion 90 of the intermediate connector 28 therein to interconnect the connector 28 (and the head 26) with the body 24 at an angle relative to the longitudinal axis L. In one embodiment, the inclination angle α is approximately 135°, and the opening 72 is at least partially threaded for threading engagement with the first end portion 90 of the connector 28. However, other inclination angles α and/or other engagement structures or mechanisms for engaging the connector 28 with the body 24 are also contemplated. Additionally, in the illustrated embodiment, the side wall 64a and the inclined proximal end wall 70 together define a projection 74 extending medially from the body 24. In the illustrated embodiment, the body 24 also defines a flange or fin 76 projecting laterally from the side wall 64b and extending along a height of the body 24 generally along the longitudinal axis L. In one embodiment, the transition between the side wall 64b and the fin 76 is curved so as to define a pair of rounded or arcuate recesses 78a, 78b positioned on either side of the fin 76, the purpose of which will be discussed below. Additionally, in the illustrated embodiment, the body 24 includes three pairs of suture anchor attachment locations 30b, 30c, 30d, with each pair positioned along various portions of the body 24 and arranged generally opposite one another along the opposite side walls 62a, 62b. However, it should be understood that the body 24 may define any number of the suture anchor attachment locations 30 along other portions of the body 24 including, for example, along the proximal end surface or the proximal end wall 70, along the side walls 64a, 64b, through the fin 76, and/or along other portions of the body 24. In other embodiments, the body 24 need not include any of the suture anchor attachment locations 30. Although a particular configuration of the body 24 has been illustrated and described herein, it should be understood that other types and configurations of the body 24 are also contemplated.

In the illustrated embodiment, the head 26 includes a generally hemi-spherical shaped outer articulation surface 80 facing away from the body 24, and a generally flat/planar underside surface 82 facing toward the body 24. The outer articulation surface 80 preferably defines a spherical segment sized and shaped similar to the outer anatomic surface of the humeral head 12 that is being replaced by the prosthetic head 26. The hemi-spherical articulation surface 80 is intended to cooperate with the natural joint face of the glenoid or with a prosthetic glenoid (not shown), and may be polished to reduce friction (and hence wear) with the glenoid or glenoid prosthesis. The plane of the underside surface 82 may geometrically intersect the outer articulation surface 80 generally along a circle having a central head axis B which intersects the apex of the hemi-spherical outer articulation surface 80. The head 26 further defines a conical or cylindrical-shaped indentation or recess 86 extending outwardly from the surface 82 generally along a connection axis C, and which is sized and shaped to receive a correspondingly shaped second end portion 92 of the connector 28 therein. In the illustrated embodiment, the connection axis C is eccentric or offset from the central head axis B. However, other embodiments are also contemplated wherein the connection axis C is generally co-axial with the central head axis B. Additionally, in the illustrated embodiment, the head 26 includes a single anchor attachment location 30e defined along the underside surface 82. However, it should be understood that the head 26 may define any number of suture anchor attachment locations 30 along other portions of the underside surface 82 and/or along other portions of the head 26. In other embodiments, the head 26 need not include any of the suture anchor attachment locations 30. Although a particular configuration of the prosthetic head 26 has been illustrated and described herein, it should be understood that other types and configurations of the head 26 are also contemplated.

In the illustrated embodiment, the intermediate connector 28 generally includes a first end portion 90, an opposite second end portion 92, and a neck or intermediate spacer portion 94 extending between the end portions 90, 92. In one embodiment, the first end portion 90 comprises a connection shaft defining external threads 96 configured for threading engagement within the threaded opening 72 in the body 24 to operatively engage the connector 28 (and the head 26) with the body 24. Additionally, in another embodiment, the second end portion 92 comprises a trunnion having a conical or cylindrical shaped outer surface 98 sized for receipt within the correspondingly shaped indentation 86 in the head 26 to operatively engage the connector 28 with the head 26. The neck 94 defines a shoulder or abutment that may engage the inclined proximal end wall 70 of the body 24 (or against another portion of the body 24) to space the head 26 at a desired distance from the body 24. As should be appreciated, the connector 28 serves to interconnect the head 26 to the body 24 and to position the head 26 at a desired position and orientation relative to the body 24. Although a particular configuration of the connector 28 has been illustrated and described herein, it should be understood that other types and configurations of connectors for interconnecting the body 24 and the head 26 are also contemplated.

Although the components of the prosthesis 20 have been illustrated and described as having a particular configuration, it should be understood that other types and configurations of the stem 22, the body 24, the head portion 26 and/or the connector 28 are also contemplated as would occur to one having ordinary skill in the art. Further details regarding prosthetic components that may be used in association with the present invention are illustrated and described in U.S. Pat. Nos. 7,758,650 and 6,749,637, the contents of which have been incorporated herein by reference in their entirety.

Referring collectively to FIGS. 3, 4, 5A, 5B and 6A-6C, further elements and features associated with the suture anchor attachment locations will now be described in greater detail. As set forth above, the suture anchor attachment locations 30 are configured for selective engagement with a suture anchor (i.e., suture anchors 40) which includes one or more sutures S extending therefrom to provide a mechanism for selective attachment of the sutures S to the prosthesis 20. As also set forth above, one or more of the suture anchor attachment locations 30 may be defined along various portions of the stem portion 22, the body portion 24 and/or the head portion 26 of the prosthesis 20. More specifically, in the illustrated embodiment, the stem 22 includes a pair of suture anchor attachment locations 30a, the body 24 includes three pairs of suture anchor attachment locations 30b, 30c and 30d, and the head 26 includes a suture anchor attachment location 30e. However, it should be understood that the prosthesis 20 may be provided with any number of suture anchor attachment locations 30 along any surface or region of the stem portion 22, the body portion 24 and/or the head portion 26. As will be discussed in greater detail below, the suture anchor attachment locations 30 provide the surgeon flexibility in selecting the optimum location(s) on the prosthesis 20 to place the suture anchor(s) 40 and the sutures S extending therefrom to repair one or more fractures of the upper extremity of the humerus 10.

Figure 5A:
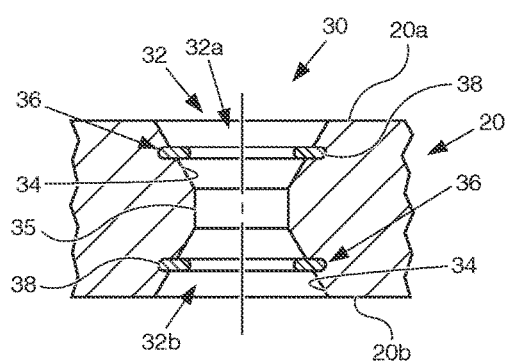
FIGS. 5A and 5B are cross-sectional views of the orthopedic prosthesis of FIG. 3, as taken along line 5-5 of FIG. 3, illustrating embodiments of an anchor seat with the suture anchor removed from the prosthesis body for clarity.
Figure 5B:
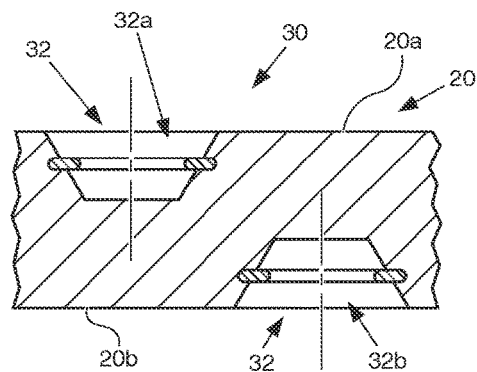

In the illustrated embodiment, the suture anchor attachment locations 30a-30e defined by the stem portion 22, the body portion 24 and the head portion 26 are configured identical to one another. However, in other embodiments, one or more of the suture anchor attachment locations 30a-30e may be provided with different configurations, including attachment locations having a different size and/or shape and/or having other types and configurations of attachment/engagement features. Referring to FIG. 5A, in the illustrated embodiment, the suture anchor attachment location 30 is configured as an opening or recess 32 extending through the prosthesis 20 to thereby form an anchor seat on each side of the prosthesis 20 for receipt of a corresponding suture anchor 40. In one embodiment, the openings/recesses 32 are pre-formed or pre-drilled in the prosthesis 20. However, in other embodiments, one or more of the openings/recesses 32 may be formed in the prosthesis 20 in-situ or intraoperatively subsequent to implantation of the prosthesis 20. In still other embodiments, the prosthesis 20 may include a plurality of indicia that indicate or mark one or more of the suture anchor attachment locations 30 for formation of the openings/recesses 32 in situ or intraoperatively subsequent to implantation of the prosthesis 20. Such indicia may include indents, colors, different materials, or any other suitable indicia for marking one or more of the suture anchor attachment locations 30. In another embodiment, the prosthesis 20 need not include indicia that indicate or mark the suture anchor attachment locations 30. Instead, the surgeon may select the suture anchor attachment locations 30 freehand for formation of the openings/recesses 32, 122.

In the embodiment illustrated in FIG. 5A, the openings/recesses 32 extend entirely through a thickness of the prosthesis 20 to thereby form a first anchor seat 32a adjacent a first side 20a of the prosthesis 20, and a second anchor seat 32b adjacent an opposite second side 20b of the prosthesis 20. However, in another embodiment illustrated in FIG. 5B, the suture anchor attachment location 30 may provided with an opening/recess 32 that extends only partly through a thickness of the prosthesis 20 and which does not extend entirely through the prosthesis 20. Additionally, in the embodiment illustrated in FIG. 5A, the pair of anchor seats 32a, 32b are arranged opposite one another in a generally symmetrical or aligned relationship. However, in another embodiment illustrated in FIG. 5B, the anchor seats 32a, 32b are offset from one another in a non-symmetrical or non-aligned relationship. In yet another embodiment, the suture anchor attachment locations 30 may provided with a single opening/recess 32 arranged on one side 20a, 20b of the prosthesis 20 (i.e., the suture anchor attachment location 30 need not necessarily include a pair of openings/recesses arranged on opposite sides 20a, 20b of the prosthesis 20). Additionally, in the illustrated embodiments of the suture anchor attachment locations, the anchor seats/openings/recesses extend along axes that are arranged substantially parallel with one another. However, in other embodiments, one or more of the anchor seats/openings/recesses may extend along an axis arranged at an oblique angle or non-parallel arrangement relative to at least one other of the anchor seats/openings/recesses.

In the illustrated embodiment, each of the anchor seats 32a, 32b and 132a, 132b includes a conically-shaped or angled inner wall 34, 134 that inwardly tapers from the outer side wall of the prosthesis 20 toward a central region of the prosthesis 20. However, in another embodiment illustrated in FIG. 6B, a suture anchor attachment location 230 may be provided which includes anchor seats 232a, 232b defined by openings/recesses 232 that each have a circular cylindrical inner wall 234. Further, in the embodiment illustrated in FIG. 5A, the openings/recesses 32 each include a cylindrical intermediate region 35 that interconnects the angled inner walls 34 of the anchor seats 32a, 32b. However, in other embodiments, the angled inner walls 34 of the anchor seats 32a, 32b may intersect/overlap one another. Additionally, although the suture anchor attachment locations illustrated and described above are configured as openings/recesses extending at least partially through various regions of the prosthesis 20, in another embodiment illustrated in FIG. 6C, a suture anchor attachment location 330 may provided which includes a stem or projections 332 extending outwardly from opposite sides 20a, 20b of the prosthesis 20 to thereby provide anchor seats 332a, 332b positioned on opposite sides of the prosthesis 20. In the illustrated embodiment, the stems/projections 332 each have a circular cylindrical configuration. However, other shapes and configurations of the stems/projections 332 are also contemplated including, for example, a conical or tapered configuration, a rectangular configuration, a hexagonal configuration, an irregular configuration, or other suitable shapes and configurations.

Referring collectively to FIGS. 3, 4, 7 and 8A-8C, further elements and features associated with the suture anchors will now be described in greater detail. As will be discussed below, the suture anchors 40 are configured for selective engagement with the suture anchor attachment locations 30 to attach the suture anchors 40 (and the sutures S) to one or more portions of the prosthesis 20. It should be understood that the sutures S may be attached to the suture anchors 40 by any suitable method or attachment technique including, for example, by threading the sutures S through one or more openings/apertures/eyes (not shown) in the anchors 40. However, other methods and techniques for attaching the sutures S to the suture anchors 40 are also contemplated including, for example, via knotting (FIGS. 11-14), a fastener, an adhesive, or other suitable methods and techniques for attaching sutures to device/structures.

Figure 7:
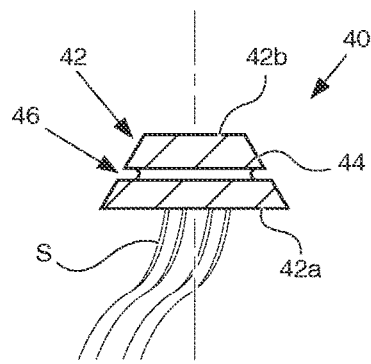
FIG. 7 is a side view of the suture anchor of FIG. 3.

As shown in FIG. 7, in the illustrated embodiment, the suture anchors 40 each include an anchor body 42 having opposite end walls 42a, 42b, and a conically-shaped or angled outer side wall 44 defining an inwardly extending taper angle from the outer end wall 42a to the inner end wall 42b that generally matches the taper angle of the openings/recesses 32 defined by the suture anchor attachment locations 30. As should be appreciated, the anchor bodies 42 of the suture anchors 40 are sized and shaped for positioning within the openings/recesses 32 of the suture anchor attachment locations 30. In the illustrated embodiment, the suture anchor body 42 has a thickness (i.e., the distance between the end walls 42a, 42b) that generally matches the depth of the opening/recess 32 such that the outer end wall 42a of the body 42 is arranged substantially flush with an outer surface of the prosthesis 20. However, it should be understood that in other embodiments, the outer end wall 42a may extend beyond or may be recessed below the outer surface of the prosthesis 20. Although the suture anchor 40 has been illustrated and described as having a particular shape and configuration, it should be understood that other shapes and configurations of suture anchors are also contemplated.

Figure 8A:
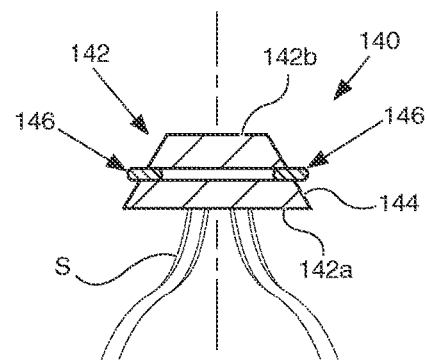
FIGS. 8A-8C are side views of other embodiments of suture anchors for use in association with the orthopedic prosthesis of FIG. 3.
Figure 8B:
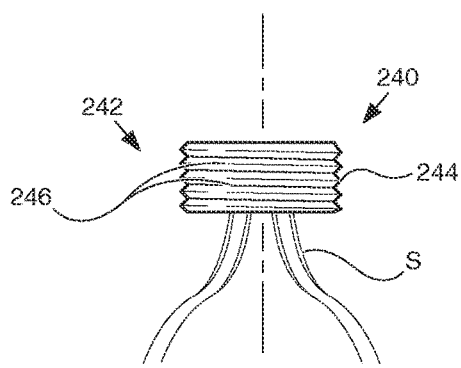

Referring to FIG. 8A, in another anchor embodiment, a suture anchor 140 is provided which includes a body 142 having a conically-shaped or angled outer wall 144 defining an inwardly extending taper angle, but which has a somewhat reduced thickness compared to the suture anchor body 42. The reduced thickness of the anchor body 142 corresponds to the shallower depth of the openings/recesses 132 defined by the suture anchor attachment location 130 illustrated in FIG. 6A. Referring to FIG. 8B, in another anchor embodiment, a suture anchor 240 is provided which includes a body 242 having a circular cylindrical configuration including a circular cylindrical outer wall 244 that generally matches the circular cylindrical configuration of the inner wall 234 defined by the openings/recesses 232 of the suture anchor attachment location 230 illustrated in FIG. 6B. Additionally, referring to FIG. 8C, in another anchor embodiment, a suture anchor 340 is provided which includes a body 342 defining an aperture 343 sized for receipt of the stem/projection 332 defined by the anchor seats 332a, 332b of the suture anchor attachment location 330 illustrated in FIG. 6C. The aperture 343 may be provided with various sizes and shapes configured for receipt of the stem/projection 332 therein including, for example, a circular cylindrical configuration, a conical or tapered configuration, a rectangular configuration, a hexagonal configuration, an irregular configuration, or other suitable shapes and configurations.

Referring collectively to FIGS. 5A and 7, in the illustrated embodiment, the suture anchor attachment location 30 is provided with one or more engagement elements 36 configured for mating engagement with a corresponding engagement element 46 defined by the suture anchor 40 to selectively retain/secure the suture anchor 40 in position relative to the suture anchor attachment location 30. In the illustrated embodiment, the engagement element 36 is configured as a projection or tongue projecting laterally from the inner wall 34 of the opening/recess 32 and sized and shaped for receipt within a corresponding recess or groove 46 defined in the outer wall 44 of the anchor body 42. In a more specific embodiment, the projection/tongue 36 is configured as a ring or annular flange sized and shaped for receipt within an annular recess/groove 38 formed in the inner wall 34 of the opening/recess 32. In one embodiment, the ring/annular flange 36 extends entirely about the inner perimeter of the opening 32. However, other embodiments are also contemplated where the ring/annular flange 36 may extend only partially about the inner perimeter of the opening 32. Additionally, although the ring/annular flange 36 is illustrated as being formed as a separate element relative to the inner wall 34 of the opening 32, it should be understood that in other embodiments, the ring/annular flange 36 may be formed integral with the inner wall 34. In a further embodiment, the ring/flange 36 is formed of a flexibly elastic material that may be partially deformed or compressed to facilitate positioning within the recess/groove 46 defined by the outer wall 44 of the suture anchor body 42, and with the ring/flange 36 reformed or expanded within the recess/groove 46 to thereby interconnect the suture anchor 40 with the suture anchor attachment location 30. However, other embodiments are also contemplated where the ring/annular flange 36 may be provided as a rigid or semi-rigid element. In one embodiment, the ring/flange 36 may be provided in the form of an annular ring, a c-clip, or an e-clip. However, it should be understood that other forms of the ring/flange are also contemplated as would occur to one having ordinary skill in the art.

Figure 6A:
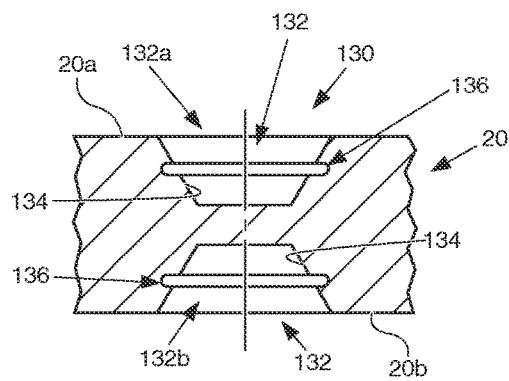
FIGS. 6A-6C are cross-sectional views illustrating other embodiments of anchor seats for use in association with the orthopedic prosthesis of FIG. 3.

Referring collectively to FIGS. 6A and 8A, in the illustrated embodiment, the suture anchor attachment location 130 is provided with one or more engagement elements 136 configured for mating engagement with a corresponding engagement element 146 defined by the suture anchor 140 to selectively retain/secure the suture anchor 140 in position relative to the suture anchor attachment location 130. In one embodiment, the engagement element 136 is configured as a recess or groove formed in the inner wall 134 of the opening/recess 132 that is sized and shaped for receipt of a corresponding projection or tongue 146 extending from the outer wall 144 of the anchor body 142. In a more specific embodiment, the recess/groove 136 is configured as an annular recess/groove sized and shaped for receipt of an annular ring/flange 146 extending from the anchor body 142. In one embodiment, the annular recess/groove 136 extends entirely about the inner perimeter of the opening 132, and the annular ring/flange 146 extends entirely about the outer perimeter of the anchor body 142. However, other embodiments are also contemplated where the annular recess/groove 136 may extend only partially about the inner perimeter of the opening 132, and/or the annular ring/flange 146 may extend only partially about the outer perimeter of the anchor body 142.

Additionally, although the ring/annular flange 146 is illustrated as being formed as a separate element relative to the outer wall 144 of the anchor body 142 for receipt within an annular recess/groove 136 formed in the opening 132, it should be understood that in other embodiments, the ring/annular flange 146 may be formed integral with the outer wall 144. In one embodiment, the ring/flange 146 is formed of a flexibly elastic material that may be partially deformed or compressed to facilitate positioning within the recess/groove 136 defined by the inner wall 134 of the opening/recess 132, and with the ring/flange 146 reformed or expanded within the recess/groove 136 to interconnect the suture anchor 140 with the suture anchor attachment location 130. However, other embodiments are also contemplated where the ring/annular flange 146 may be provided as a rigid or semi-rigid element. In still other embodiments, the anchor body 142 may be provided with a pair of flexible legs or arms separated from one another by a slot wherein the legs/arms may be flexibly deformed toward one another for receipt within the opening/recess 132 of the attachment location 130, and with the legs/arms resiliently returning toward their initial undeformed configuration to capture/retain the anchor body 142 within the opening/recess 132 to thereby selectively engage the suture anchor 140 with the attachment location 130. In still other embodiments, one or more portions of the attachment location 130 and/or the suture anchor 140 may be formed of a shape-memory or superelastic material such as, for example, a shape-memory alloy or a shape-memory polymer, which changes shape upon the removal of stress or a corresponding change in temperature to capture/retain the suture anchor 140 with the attachment location 130. In one embodiment, the ring/flange 146 may be provided in the form of an annular ring, a c-clip, or an e-clip. However, it should be understood that other forms of the ring/flange are also contemplated as would occur to one having ordinary skill in the art. Additionally, as discussed above in association with FIGS. 5A and 7, the suture anchor attachment locations 30 may be provided with a ring/flange 36 positioned within an annular recess/groove 38 formed in the inner wall 34 of the opening/recess 32, with the ring/flange 36 positioned within a recess/groove 46 defined by the outer wall 44 of the suture anchor body 42 to selectively attach the suture anchor to the prosthesis body.

Figure 6B:
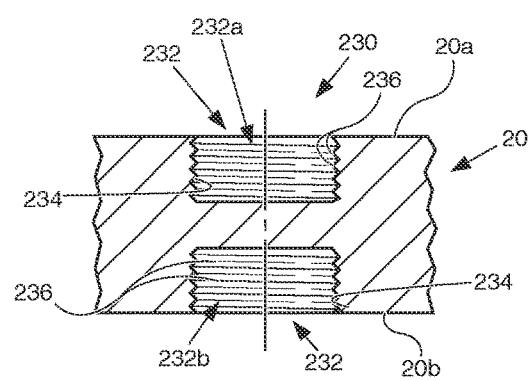

Referring collectively to FIGS. 6B and 8B, in the illustrated embodiment, the suture anchor attachment location 230 is provided with one or more engagement elements 236 configured for mating engagement with a corresponding engagement element 246 defined by the suture anchor 240 to selectively retain/secure the suture anchor 240 in position relative to the suture anchor attachment location 230. In the illustrated embodiment, the engagement element 236 is configured as internal threads formed along the inner wall 234 of the opening/recess 232 which are configured for threading engagement with corresponding external threads 246 formed along the outer wall 244 of the anchor body 242. However, other embodiments are also contemplated where the mating internal/external threads 236, 246 may be replaced with other types and configurations of mating engagement elements including, for example, ratchet/ratcheting elements, snap-in engagement elements, frictional engagement elements, interference-type elements, or other suitable types of engagement elements configured to selectively engage the suture anchor 240 with the suture anchor attachment location 230.

Figure 6C:
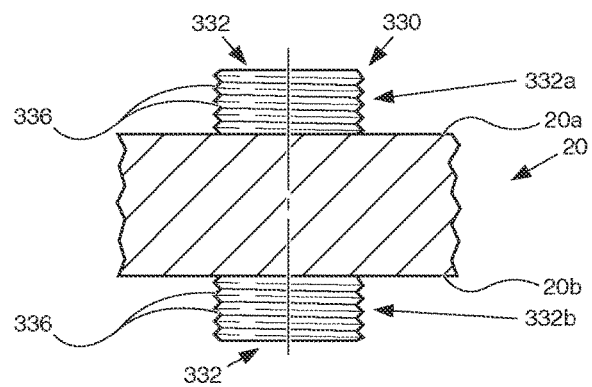
Figure 8C:
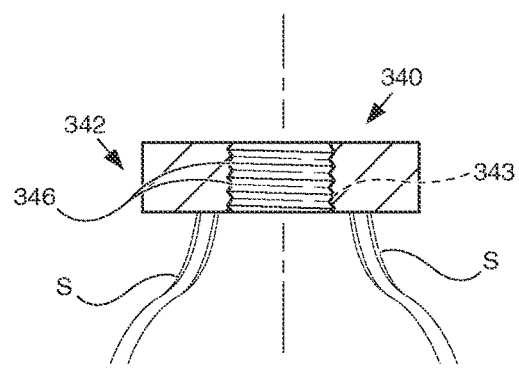

Referring collectively to FIGS. 6C and 8C, in the illustrated embodiment, the suture anchor attachment location 330 is provided with one or more engagement elements 336 configured for mating engagement with a corresponding engagement element 346 defined by the suture anchor 340 to selectively retain/secure the suture anchor 340 in position relative to the suture anchor attachment location 330. In the illustrated embodiment, the engagement element 336 is configured as external threads formed along the outer wall 334 of the stem/projection 332 which are configured for threading engagement with corresponding internal threads 346 formed along the inner wall 344 of the aperture 343 in the anchor body 342. However, other embodiments are also contemplated where the mating external/internal threads 336, 346 may be replaced with other types and configurations of mating engagement elements including, for example, tongue/groove elements, ratchet/ratcheting elements, snap-in engagement elements, frictional engagement elements, interference-type elements, or other suitable types of engagement elements configured to selectively engage the suture anchor 340 with the suture anchor attachment location 330.

As should be appreciated from the embodiments illustrated in FIGS. 5A, 5B, 6A-6C, 7 and 8A-8C and the corresponding descriptions set forth above, numerous structures/elements/techniques are available for selectively engaging the suture anchors with the suture anchor attachment locations. However, it should be understood that these embodiments are exemplary in nature, and that other suitable structures/elements/techniques may be provided for selectively engaging the suture anchors with the suture anchor attachment locations. Additionally, in one embodiment, selective engagement of the suture anchors with the suture anchor attachment locations results in a rigid interconnection between the suture anchors and the prosthesis 20. However, other embodiments are also contemplated wherein selective engagement of the suture anchors with the suture anchor attachment locations results in a semi-rigid, flexible or dynamic interconnection between the suture anchors and the prosthesis 20.

Referring now to FIGS. 9 and 10, reference will now be made to use of the prosthesis 20 to repair one or more fractures of the upper extremity of the humerus 10 according to one form of the present invention. However, it should be understood that the disclosed use is exemplary in nature, and that other uses of the prosthesis 20 are also contemplated as falling within the scope of the present invention.

As discussed above, in a traumatic accident, the upper extremity of the humerus 10 may break into several fragments along multiple fracture lines, with the humeral head separating from the upper extremity of the humerus 10 along a fracture line $F_1$ at or near the anatomical neck, the greater tuberosity 14 separating from the lesser tuberosity 16 along a fracture line $F_2$ at or near the biciptal groove, and/or the humeral shaft 18 separating along a fracture line $F_3$ at or near the surgical neck. Attached to the displaced tuberosity fragments are muscles and tendons of the rotator cuff (not shown). When the humeral head fragment is significantly displaced or damaged, the surgeon may choose to remove the anatomical humeral head fragment and replace it with the prosthetic head portion 26 of the prosthesis 20. The prosthetic head portion 26 is attached to the body portion 24, which is in turn attached to the stem portion 22. The stem portion 22 is embedded/anchored within the humeral shaft 18 to operatively attach the prosthesis 20 to the humerus 10, the details of which would be apparent to one having ordinary skill in the art.

Following anchoring of the stem portion 22 within the humeral shaft 18, the greater and lesser tuberosity fragments 14, 16 are displaced to their proper anatomic position/orientation about the body portion 24 of the prosthesis 20 beneath the head portion 28 and into proper anatomic alignment with the humeral shaft 18. The greater and lesser tuberosity fragments 14, 16 may be placed in compressed engagement against the humeral shaft 18 and/or against one another via the sutures S, further details of which will be set forth below. As shown in FIG. 10, the body portion 24 of the prosthesis 20 includes a flange or fin 76 projecting laterally therefrom and defining a pair of rounded or arcuate recesses or curved surfaces 78a, 78b on either side of the fin 76. Corresponding portions of the greater and lesser tuberosity fragments 14, 16 are positioned in abutment against the arcuate recesses or curved surfaces 78a, 78b to aid in reducing the fragments 14, 16 to their proper anatomic position/orientation and/or to provide further stabilization and support to the fragments 14, 16.

The location of the sutures S may be optimized to help facilitate the application of compression forces in the direction of arrows $C_1$ to reduce the tuberosity fragments 14, 16 to their proper anatomic position/orientation relative to one another for improved healing, and to help facilitate application of compression forces in the direction of arrows $C_2$ to reduce the tuberosity fragments 14, 16 to their proper anatomic position/orientation relative to the humeral shaft 18 for improved healing. As should be appreciated, the surgeon can quickly and easily select the proper suture anchor attachment locations 30 (i.e., attachment locations 30a-30e) that will result in draping of the sutures S to achieve optimal placement and organization of the sutures S relative to the tuberosity fragments 14, 16 and the humeral shaft 18. In one embodiment, the suture anchors 40 are attached to select ones of the suture anchor attachment locations 30 in-situ or intraoperatively subsequent to implantation of the prosthesis 20 (i.e., subsequent to attachment of the prosthesis to the humerus). However, in other embodiments, the suture anchors 40 may be pre-attached to select ones of the suture anchor attachment locations 30 prior to implantation of the prosthesis 20. Additionally, in one embodiment, the sutures S may be engaged to corresponding ones of the suture anchors 40 in-situ or intraoperatively subsequent to implantation of the prosthesis 20. However, in other embodiments, the suture anchors 40 may be pre-engaged or pre-loaded to the suture anchors 40 prior to implantation of the prosthesis 20. In a further embodiment, a number of plugs or inserts may be provided to cover any unused openings/recesses 32 of the suture anchor attachment locations 30 (i.e., to cover the openings/recesses 32 that are not engaged with one of the suture anchors 40).

In a further aspect of the invention, the sutures S may be provided with anatomy based color-coding or other types of indicia-coding. For example, the sutures S can be color coded to correspond to a particular portion of the humerus 10 (i.e., tuberosity fragments 14, 16 and humeral shaft 18) and/or to a particular fracture line (i.e., fracture lines $F_2$ and $F_3$). For example, a first group of sutures $S_1$ of a first color may be provided for use in association with the greater tuberosity fragment 14, a second group of sutures $S_2$ of a second color may be provided for use in association with the lesser tuberosity fragment 16, and a third group of sutures $S_3$ of a third color may be provided for use in association with the humeral shaft 18. In one exemplary embodiment, three pairs of red sutures $S_1$ may be provided for use in association with the greater tuberosity fragment 14, three pairs of green sutures $S_2$ may be provided for use in association with the lesser tuberosity fragment 16, and two pairs of white sutures $S_3$ may be provided for use in association with the humeral shaft 18. However, it should be understood that any number of sutures S may be utilized in association with various bone fragments and/or fracture lines, and that other suture colors are also contemplated for use in association with the present invention. Additionally, the colored sutures S need not necessarily define a solid color. For example, in one embodiment, one or more of the suture S may be formed of a plurality of white suture threads/strands interwoven or integrated with a colored (i.e., non-white) tracer thread/strand. It should also be understood that the suture anchors 40 may be provided with anatomy based color-coding or other types of indicia-coding, in addition to or in lieu of anatomy based coding of the sutures S. Additionally, it should further be understood that the sutures S and/or the suture anchors 40 may be provided with other types of indicia-coding other than color including, for example, various types of markings or markers associated with specific suture groups.

Following attachment of the suture anchors 40 to select ones of the suture anchor attachment locations 30 and draping of the sutures S (i.e., color-coded suture groups $S_1$, $S_2$ and $S_3$) to properly position and organize the sutures S relative to the prosthesis 20 and the anatomy of the humerus 10, the sutures S are engaged/tied to the tuberosity fragments 14, 16 and the humeral shaft 18 to facilitate compression and reduction of the bone fragments in the direction of arrows $C_1$ and $C_2$ to thereby reduce the tuberosity fragments 14, 16 to their proper anatomic position relative to one another and relative to the humeral shaft 18. As should be appreciated, the present invention may reduce the overall length and complexity of the surgical procedure to repair humeral fractures (or other types of fractures) compared to conventional surgical repair techniques. As should be further appreciated, the present invention provides the surgeon with the flexibility of selecting locations for attachment of the sutures S from multiple locations on the prosthesis 20. Additionally, the present invention simplifies reduction of the tuberosity fragments 14, 16 to their proper anatomic position/orientation, and also facilitates optimal compression between the tuberosity fragments 14, 16 to improve healing. As should be further appreciated, the present invention may improve post-operative arm/shoulder function, which is directly correlated to restoration of proper tension in the rotator cuff, and proper tension in the rotator cuff is directly correlated to anatomical reconstruction/reduction of the tuberosity fragments 14, 16 and successful healing of the tuberosity fragments 14, 16 to each other and to the humeral shaft 18.

Figure 11:
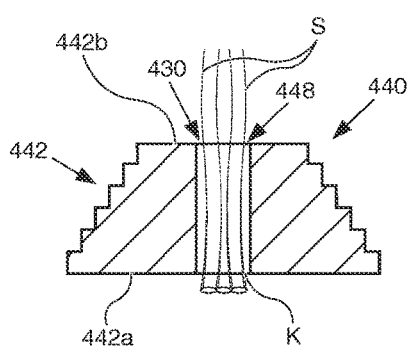
FIG. 11 is a partial cross-sectional view of a portion of another embodiment of an orthopedic prosthesis including a suture seat for use in association with the present invention.

Referring to FIG. 11, shown therein is a partial cross-sectional view of a portion 440 of an orthopedic prosthesis including at least one suture attachment location 430 for use in association with the present invention. As will be appreciated, the suture attachment location 430 is configured for direct engagement with a portion of the sutures S (i.e., without the use of a suture anchor 40). In the illustrated embodiment, the prosthesis portion 440 is configured for direct engagement with or abutment against a knotted portion K of the sutures S to operatively attach the sutures S to the prosthesis portion 440. However, in other embodiments, the sutures S may be operatively attached to a suture anchor via a technique similar to that described below, and with the suture anchor in turn selectively engaged with a suture anchor attachment location defined by the prosthesis to operatively attach the sutures S to the prosthesis.

In the illustrated embodiment, the prosthesis portion 440 includes a body 442 having opposite side walls 442a, 442b, and a through opening 448 extending between the opposite side walls 442a, 442b for receipt of the sutures S therethough, with the knotted portion K of the sutures S abutting one of the side walls 442a, 442b of the body 442 to prevent the knotted suture portion K from passing entirely through the opening 448. The knotted portion K of the sutures S may be formed using any suitable method or technique to provide the knotted suture portion K with an outer dimension somewhat larger than the minimum inner dimension of the opening 448. In one embodiment, the free ends of the sutures S are threaded through the opening 448 from the side wall 442a and pulled through the opening 448 until the knotted suture portion K is positioned in abutment against the outer side wall 442a to prevent the knotted suture portion K from passing entirely through the opening 448, thereby operatively attaching the sutures S to the prosthesis portion 440. In another embodiment, the free ends of the sutures S may be threaded through the opening 448 from the side wall 442b and pulled through the opening 448 until the knotted suture portion K is positioned in abutment against the side wall 442b to prevent the knotted suture portion K from passing entirely through the opening 448. In still another embodiment, free ends of the sutures S may threaded through the opening 448 until positioned beyond one of the side walls 442a, 442b, and the free ends are knotted or operatively expanded to form the knotted suture portion K which is in turn pulled into abutment against the side wall to operatively attach the sutures S to the prosthesis portion 440. As indicated above, the knotted suture portion K may be formed using any suitable method or technique known to those having ordinary skill in the art.

Figure 12A:
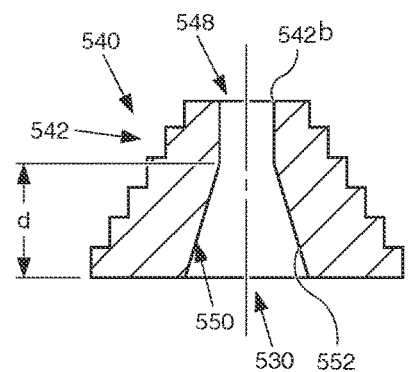
FIGS. 12A-12C are partial cross-sectional views of a portion of other embodiments of orthopedic prostheses including a suture seat for use in association with the present invention.
Figure 12B:
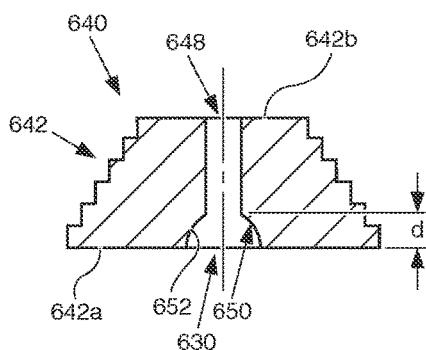
Figure 12C:
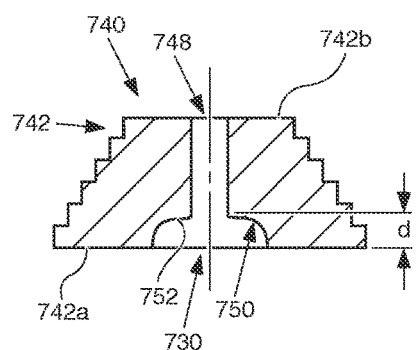

Referring to FIGS. 12A-12C, shown therein are partial cross-sectional views of portions 540, 640, 740 of an orthopedic prosthesis, each including at least one suture attachment location for use in association with the present invention. In the illustrated embodiments, the prostheses portions 540, 640, 740 are each configured for engagement with a knotted portion K of the sutures S, with the knotted portion K at least partially recessed below a side surface of the prostheses portion 540, 640, 740 to reduce the likelihood of suture breakage. More specifically, each of the prosthesis portions 540, 640, 740 includes a recessed or countersunk region having a depth d sized for receipt of the knotted portion K of the sutures S to protect/shield the knotted portion K to reduce the likelihood of suture breakage. Additionally, it should be appreciated that the sutures S may be operatively attached to the prosthesis portions 540, 640, 740 prior to implantation of the prosthesis, or may alternatively be operatively attached to the prosthesis portion after implantation of the prosthesis. It should also be appreciated that attachment of the sutures S to the prosthesis portions 540, 640, 740 does not require the use of a suture anchor. Instead, the sutures S are operatively attached to the prosthesis portions 540, 640, 740 via abutment of the knotted suture portion K directly against the body of the prosthesis portion. However, in other embodiments, the sutures S may be operatively attached to a suture anchor via a technique similar to that illustrated and described above with regard to attachment of the sutures S to the prosthesis portions, and with the suture anchor in turn selectively engaged with a suture anchor attachment location defined by the prosthesis.

Referring to FIG. 12A, the prosthesis portion 540 is configured similar to the prosthesis portion 440 illustrated and described above and includes at least one suture attachment location 530. The prosthesis portion 540 includes a body 542 having opposite side walls 542a, 542b, and a through opening 548 extending between the opposite side walls 542a, 542b for receipt of the sutures S therethrough. However, the prosthesis portion 540 includes a conically shaped recess or countersunk region 550 extending from the side wall 542a and having a depth d sized for receipt of the knotted portion K of the sutures S therein such that the knotted suture portion K is positioned substantially flush with or recessed at least partially below the side wall 542a of the prosthesis portion 540. In another embodiment, the conically shaped recess or countersunk region 550 may alternatively extend from the side wall 542b. As should be appreciated, the free ends of the sutures S may be threaded through the opening 548 from the side wall 542a and pulled through the opening 548 until the knotted suture portion K is positioned in abutment against the angled/tapered surface 552 defined by the countersunk region 550 to prevent the knotted suture portion K from passing entirely through the opening 548, thereby operatively attaching the sutures S to the prosthesis portion 540. In another embodiment, free ends of the sutures S may threaded through the opening 548 from the side wall 542b until positioned beyond the side walls 542a, and the ends are knotted or operatively expanded to form the knotted suture portion K which is in turn pulled into abutment against the angled/tapered surface 552 of the countersunk region 550 to operatively attach the sutures S to the prosthesis portion 540.

Referring to FIG. 12B, the prosthesis portion 640 is also configured similar to the prosthesis portion 440 illustrated and described above and includes at least one suture attachment location 630. The prosthesis portion 640 includes a body 642 having opposite side walls 642a, 642b, and a through opening 648 extending between the opposite side walls 642a, 642b for receipt of the sutures S therethrough. However, the prosthesis portion 640 includes a semi-spherical shaped recess or countersunk region 650 extending from the side wall 642a and having a depth d sized for receipt of the knotted portion K of the sutures S therein such that the knotted suture portion K is positioned substantially flush with or recessed at least partially below the side wall 642a of the prosthesis portion 640. In another embodiment, the semi-spherical shaped recess or countersunk region 650 may alternatively extend from the side wall 642b. As should be appreciated, the free ends of the sutures S may be threaded through the opening 648 from the side wall 642a and pulled through the opening 648 until the knotted suture portion K is positioned in abutment against the curved surface 652 defined by the countersunk region 650 to prevent the knotted suture portion K from passing entirely through the opening 648, thereby operatively attaching the sutures S to the prosthesis portion 640. In another embodiment, free ends of the sutures S may threaded through the opening 648 from the side wall 642b until positioned beyond the side walls 642a, and the ends are knotted or operatively expanded to form the knotted suture portion K which is in turn pulled into abutment against the curved surface 652 of the countersunk region 650 to operatively attach the sutures S to the prosthesis portion 640.

Referring to FIG. 12C, the prosthesis portion 740 is likewise configured similar to the prosthesis portion 440 illustrated and described above and includes at least one suture attachment location 730. The prosthesis portion 740 includes a body 742 having opposite side walls 742a, 742b, and a through opening 748 extending between the opposite side walls 742a, 742b for receipt of the sutures S therethrough. However, the prosthesis portion 740 includes a circular-shaped recess or countersunk region 750 extending from the side wall 742a and having a depth d sized for receipt of the knotted portion K of the sutures S therein such that the knotted suture portion K is positioned substantially flush with or recessed at least partially below the side wall 742a of the prosthesis portion 740. In another embodiment, the circular-shaped recess or countersunk region 750 may alternatively extend from the side wall 742b. In other embodiments, the recess or countersunk region 750 may be provided with other shapes and configurations including, for example, a hexagonal or star shaped configuration, or any other suitable shape or configuration. As should be appreciated, the free ends of the sutures S are threaded through the opening 748 from the side wall 742a and pulled through the opening 748 until the knotted suture portion K is positioned in abutment against the bottom surface or shoulder 752 defined by the countersunk region 750 to prevent the knotted suture portion K from passing entirely through the opening 748, thereby operatively attaching the sutures S to the prosthesis portion 740. In another embodiment, free ends of the sutures S may threaded through the opening 748 from the side wall 742b until positioned beyond the side walls 742a, and the ends are knotted or operatively expanded to form the knotted suture portion K which is in turn pulled into abutment against the shoulder 752 of the countersunk region 750 to operatively attach the sutures S to the prosthesis portion 740.

Figure 13:
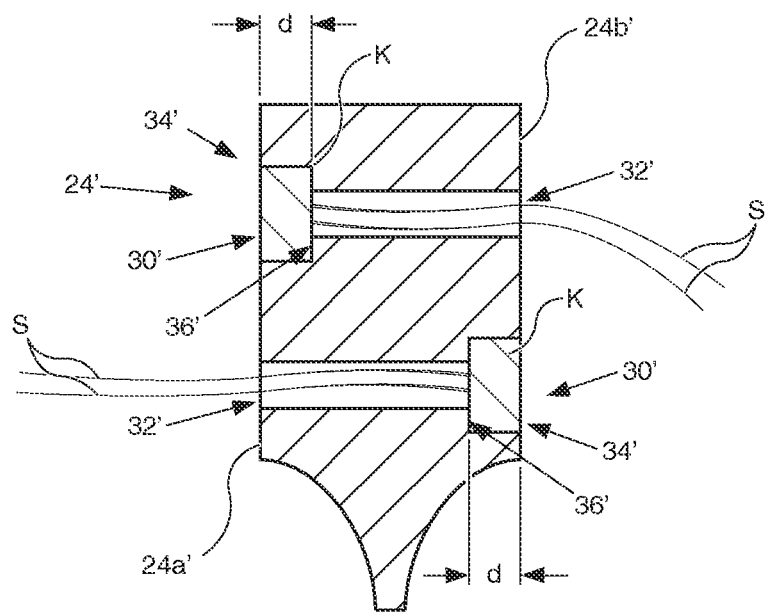
FIG. 13 is a cross-sectional view of the upper body portion of an orthopedic prosthesis according to another form of the present invention.

Referring to FIG. 13, shown therein is a body portion 24' for use in association with the orthopedic prosthesis 20 according to another embodiment of the present invention. The body portion 24' is configured similar to the body portion 24 illustrated and described above. However, the body portion 24' includes suture attachment locations 30' that are configured somewhat differently from the suture anchor attachment locations 30 associated with the body portion 24. Specifically, unlike the suture anchor attachment locations 30 associated with the body portion 24 which are configured for selective engagement with a suture anchor 40 including one or more sutures S extending therefrom, the suture attachment locations 30' are configured for direct engagement with a portion of the sutures S (i.e., without the use of a suture anchor 40).

In the illustrated embodiment, the body portion 24' includes opposite side walls 24a', 24b', and the suture attachment locations 30' each include a through opening 32' extending between the opposite side walls 24a', 24b' for receipt of the sutures S therethrough. Additionally, the through openings 32' each include a circular-shaped recess or countersunk region 34' extending from opposite ones of the side walls 24a', 24b' and defining a lower surface or shoulder 36' to provide the countersunk region 34' with a depth d sized for receipt of the knotted portion K of the sutures S therein. The knotted suture portion K is preferably positioned substantially flush with or recessed at least partially below the side walls 24a', 24b' of the body portion 24' to protect/shield the knotted suture portion K and reduce the likelihood of suture breakage. In other embodiments, the recess or countersunk region 34' may have other shapes and configurations including, for example, a conical configuration, a semi-spherical configuration, a hexagonal or star shaped configuration, or any other suitable shape or configuration. The knotted portion K of the sutures S may be formed using any suitable method or technique to provide the knotted suture portion K with an outer dimension somewhat larger than the minimum inner dimension of the opening 32'. In one embodiment, the free ends of the sutures S may be threaded through the countersunk region 34' and pulled through the opening 32' until the knotted suture portion K is positioned within the countersunk region 34' in abutment against the shoulder 36' to prevent the knotted suture portion K from passing entirely through the opening 32', thereby operatively attaching the sutures S to the body portion 24' without the use of a suture anchor. In another embodiment, free ends of the sutures S may threaded through the opening 32' from the side wall opposite the countersunk region 34' until positioned beyond the countersunk region 34', and the ends are knotted or operatively expanded to form the knotted suture portion K which is in turn pulled into abutment against the shoulder 36' of the countersunk region 34' to operatively attach the sutures S to the body portion 24'.

Figure 14:
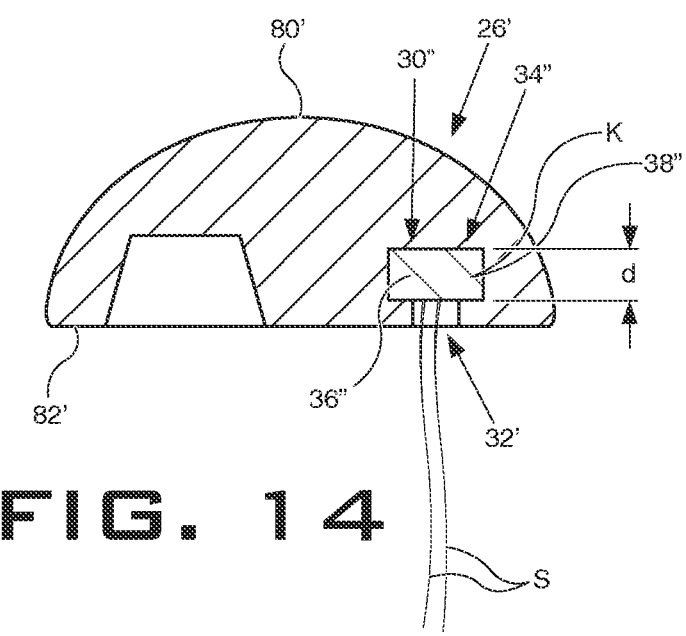
FIG. 14 is a cross-sectional view of the head portion of an orthopedic prosthesis according to another form of the present invention.

Referring to FIG. 14, shown therein is a head portion 26' for use in association with the orthopedic prosthesis 20 according to another embodiment of the present invention. The head portion 26' is configured similar to the head portion 26 illustrated and described above. However, the head portion 26' includes a suture attachment location 30" that is configured differently from the suture anchor attachment location 30 associated with the head portion 26. Specifically, unlike the suture anchor attachment location 30 associated with the head portion 26 which is configured for selective engagement with a suture anchor 40 including one or more sutures S extending therefrom, the suture attachment location 30" is configured for direct engagement with a portion of the sutures S (i.e., without the use of the suture anchor 40).

In the illustrated embodiment, the head portion 26' includes a generally hemi-spherical shaped outer articulation surface 80' and a generally flat/planar underside surface 82'. Additionally, the suture attachment location 30" is defined by a blind opening 32" extending partially through the head portion 26' from the underside surface 82' for receipt of the sutures S therein. The blind opening 32" includes a circular-shaped recess or undercut region 34" inwardly offset from the underside surface 82' and defining a bottom surface 36" and an intermediate surface or shoulder 38" to thereby provide the undercut region 34" with a depth d sized for receipt of the knotted portion K of the sutures S therein. As should be appreciated, the undercut region 34" of the blind opening 32" serves to retain the knotted suture portion K in engagement with the head portion 26', and also serves to protect/shield the knotted suture portion K to reduce the likelihood of suture breakage. In the illustrated embodiment, the blind opening 32" and the undercut region 34" each have a generally circular configuration. However, other suitable shapes and configurations of the blind opening 32' and the undercut region 34" are also contemplated. As indicated above, the knotted portion K of the sutures S may be formed using any suitable method or technique to provide the knotted suture portion K with an outer dimension somewhat larger than the minimum inner dimension of the blind opening 32". In one embodiment, the knotted suture portion K is inserted through the blind opening 32" until positioned within the undercut region 34", and is thereafter pulled into abutment against the shoulder 38" to prevent the knotted suture portion K from exiting the blind opening 32", thereby operatively attaching the sutures S to the head portion 26' without the use of a suture anchor. In another embodiment, free ends of the sutures S may threaded through the blind opening 32" from the undersurface of the head portion 26' until positioned within the undercut region 34", and the ends may be knotted or operatively expanded to form the knotted suture portion K which is in turn pulled abutment against the shoulder 38" to prevent the knotted suture portion K from exiting the blind opening 32".

Figure 15:
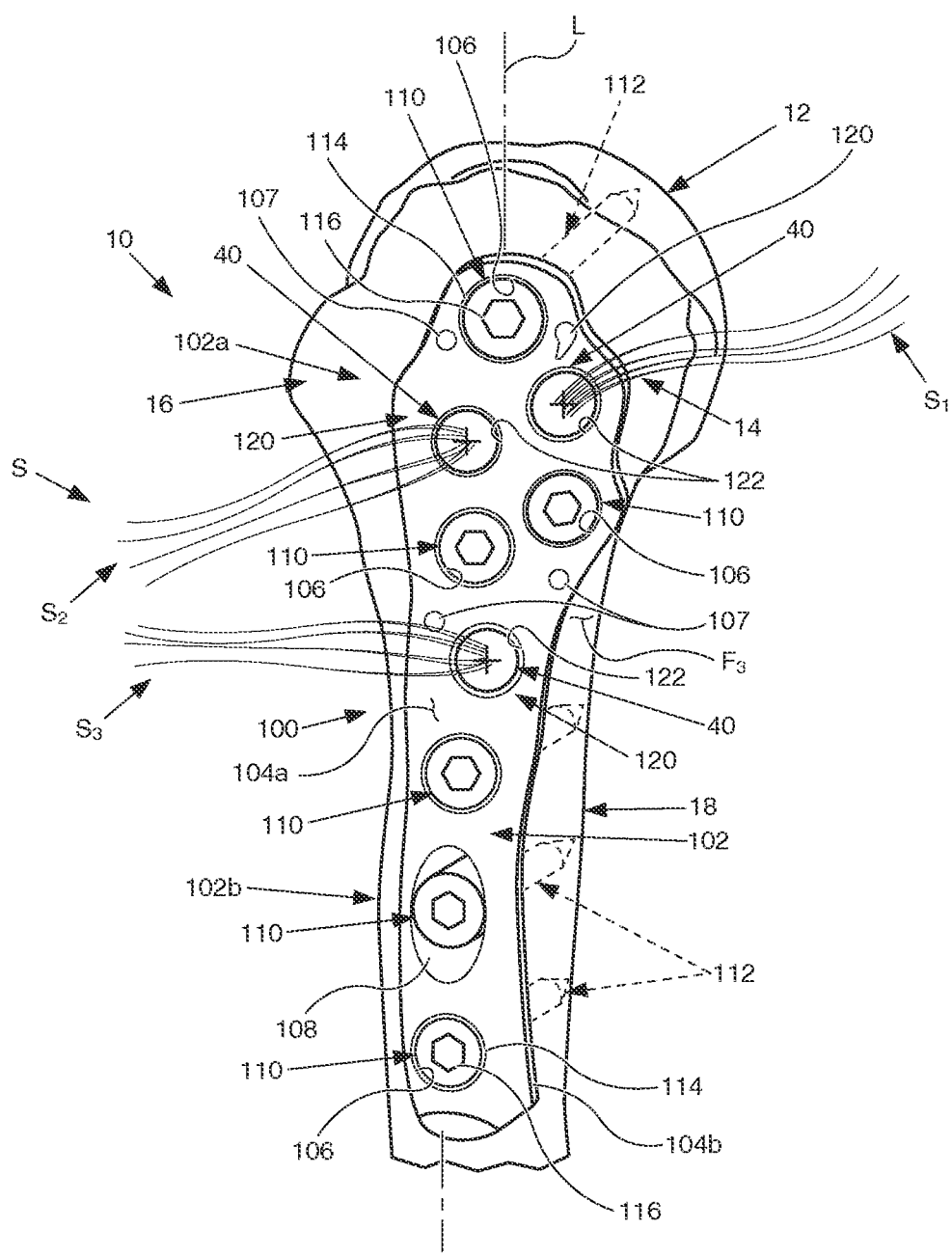
FIG. 15 is a perspective view of an orthopedic prosthesis according to another form of the present invention.

Referring to FIG. 15, shown therein is an orthopedic prosthesis 100 according to another form of the present invention. In the illustrated embodiment, the orthopedic prosthesis 100 is configured as a humeral plate for use in association with the repair of fractures of the upper extremity of the humerus 10. However, it should be understood that the orthopedic prosthesis 100 may be used in association with other bones and joints such as, for example, the hip and knee, and/or in other orthopedic surgeries and procedures. The humeral plate 100 includes an elongate plate body 102 extending generally along a longitudinal axis L, a number of bone anchors or fasteners 110 extending from the elongate plate body 102 and configured for engagement with bone tissue to attach the plate body 102 to the bone, and a number of suture anchor attachment locations 120 configured for selective engagement with one or more of the suture anchors 40 (or suture anchors 140, 240 and 340) to selectively attach the sutures S extending from the suture anchors to the plate body 102.

The components of the humeral plate 100 including the plate body 102 and the bone anchors 110 may be formed of metallic materials (i.e., stainless steel, titanium, metal alloys), polymeric materials (i.e., PEEK or other high strength polymers, copolymers or plastic materials), and/or other suitable materials known to those having ordinary skill in the art. Additionally, as discussed above, the suture anchors 40 may likewise be formed of metallic, polymeric, and/or other suitable materials which may be the same as or different from the material from which other portions of the humeral plate 100 are formed. The sutures S may be formed of synthetic materials including various polymers, biological materials, and/or other suitable suture materials known to those having ordinary skill in the art. Additionally, the sutures S may be formed of absorbable or non-absorbable materials. Further details regarding the humeral plate 100 will now be discussed in greater detail.

In the illustrated embodiment, the elongate plate body 102 includes a proximal plate/head portion 102a, a distal plate/shaft portion 102b, an upper surface 104a, an opposite lower surface 104b shaped and contoured for engagement with an outer surface of the humerus 10, and a number of openings 106, 108 extending through the plate body 102 and sized and configured for receipt of the bone anchors 110. In one embodiment, the proximal plate portion or head 102a is sized and shaped for positioning along the upper extremity of the humerus 10, and more specifically along a superior aspect of the greater tuberosity 14, and the distal plate portion or shaft 102b is sized and shaped for positioning along the humeral shaft 18. In the illustrated embodiment, the elongate plate body 102 is configured as a single-piece, monolithic structure. However, other embodiments are also contemplated where the elongate plate body 102 may have a modular configuration such as, for example, embodiments where the proximal plate portion 102*a* and the distal plate portion 102*b* constitute separate elements or plate components that are selectively connected to one another to provide an integrated, multi-piece plate body 102. Additionally, one or both of the plate portions 102*a*, 102*b* may include features configured for selective engagement or connection with other structures such as, for example, cables, rods, tethers or other types of ancillary elements or structures. For example, in one embodiment, one or both of the plate portions 102*a*, 102*b* may be provided with a groove, slot or through-opening sized to receive a cable or tether to selective engage the cable/tether with the plate body 102. Further, the lower surface 104*b* of one or both of the plate portions 102*a*, 102*b* may be contoured to fit the outer contour of the bone surface. Additionally, the lower surface 104*b* of one or both of the plate portions 102*a*, 102*b* may be recessed to permit blood flow within a gap between the lower surface 104*b* and the outer surface of the bone.

In the illustrated embodiment, each of the plate portions 102*a*, 102*b* includes at least one of the openings 106, 108 extending therethrough for receipt of corresponding ones of the bone anchors 110. In one embodiment, the proximal plate portion 102*a* includes three of the openings 106 and the distal plate portion 102*b* includes two of the openings 106, with each of the openings 106 having a generally circular configuration. Additionally, the distal plate portion 102*b* includes one of the openings 108 having a slotted configuration defining a slot length extending generally along the longitudinal axis L. However, it should be understood that the proximal and distal plate portions 102*a*, 102*b* may include any number of the openings having other suitable shapes and configurations. In a further embodiment, the openings 106, 108 may be provided with a countersink or counterbore region sized for receipt of a head portion of the bone anchor 110 therein such that the end surface of the head portion is substantially flush with or recessed slightly below the upper surface 104*a* of the plate body 102. Additionally, it should be understood that the openings 106, 108 may be provided with a locking configuration to facilitate secure engagement with a bone anchor to prevent movement of the bone anchor relative to the plate body, a non-locking configuration, or any other configuration suitable for receipt of a bone anchor. In the illustrated embodiment, the openings 106 have a generally circular configuration and the opening 108 has an elongate slotted configuration. However, other embodiments are also contemplated where the openings 106 may have a non-circular configuration and/or the opening 108 may be provide with circular portions arranged at one or both ends of the elongate slot. Additionally, one or both of the plate portions 102*a*, 102*b* may be provided with a number of provisional fixation holes 107 sized and configured for receipt of pins or fasteners (not shown) to provisionally attach the plate body 102 to bone prior to terminal anchoring of the plate body 102 to the bone via the bone anchors 110.

In the illustrated embodiment, the proximal plate portion 102*a* includes two of the suture anchor attachment locations 120, and the distal plate portion 102*b* includes one of the suture anchor attachment locations 120. However, it should be understood that the proximal and distal plate portions 102*a*, 102*b* may include any number of the suture anchor attachment locations 120. It should be further understood that the number and position of the suture anchor attachment locations 120 is exemplary, and that the plate body 102 may define any number of suture anchor attachment locations 120 along other portions of the plate body 102. Additionally, although a particular configuration of the plate body 102 has been illustrated and described herein, it should be understood that other types and configurations of the plate body 102 are also contemplated.

In the illustrated embodiment, the bone anchors 110 are configured as bone screws including a threaded shank portion 112 extending through corresponding ones of the openings 106, 108 in the plate body 102 and projecting from the lower surface 104*b* of the plate body 102 for engagement within bone tissue, and a head portion 114 positioned within the countersunk region of the openings 106, 108 (or alternatively against the upper surface 104*a*) to engage the plate body 102 to the humerus 10. The head portion 114 may be provided with a recess 116 sized and shaped for engagement with a driving tool to facilitate driving engagement of the bone anchors 110 in the bone tissue. In the illustrated embodiment, the recess 116 has a hexagonal shape. However, other suitable shapes and configurations or the recess 116 are also contemplated. Additionally, although the bone anchors 110 have been illustrated and described as bone screws, it should be understood that other suitable types and configurations of bone anchors are also contemplated including, for example, pins, staples, clamps, straps, tethers, sutures, or any other types of bone anchors or fasteners suitable for attachment of the plate body 102 to bone tissue.

In one embodiment, the suture anchor attachment locations 120 are configured similar to the suture anchor attachment locations 30 illustrated and described above with regard to the prosthesis 20. Specifically, the suture anchor attachment locations 120 are configured for selective engagement with a suture anchor 40 having one or more sutures S extending therefrom to provide a mechanism for selective attachment of the sutures S to the plate prosthesis 100. Additionally, as also set forth above, a number of the suture anchor attachment locations 120 may be defined along the proximal plate portion 102*a* and the distal plate portion 102*b*. However, it should be understood that the plate prosthesis 100 may be provided with any number of suture anchor attachment locations 120 along other portions or regions of the plate body 102. Additionally, in other embodiments, one or more of the suture anchor attachment locations 120 may be defined by the head portions 114 of the bone anchors 110, whereby the bone anchors 110 may serve as both a mechanism for attaching the plate body 102 to the humerus 10 and a mechanism for selective attachment of the suture anchors 40 to the plate body 102. As should be appreciated, the suture anchor attachment locations 120 provide the surgeon flexibility in selecting the optimum location(s) on the plate prosthesis 100 to place the suture anchors 40 and the sutures S.

In the illustrated embodiment, the suture anchor attachment locations 120 defined by the plate prosthesis 100 are configured identical to one another. However, in other embodiments, one or more of the suture anchor attachment locations 120 may be provided with different configurations, including attachment locations having a different size and/or shape and/or having other types of attachment features. In the illustrated embodiment, the suture anchor attachment locations 120 are each configured as an opening or recess 122 extending at least partially through the plate body 102 to thereby form an anchor seat for receipt of a corresponding one of the suture anchors 40. In one embodiment, the openings/recesses 122 are pre-formed or pre-drilled in the plate body 102. However, in other embodiments, one or more of the openings/recesses 122 may be formed in the plate body 102 in-situ or intraoperatively subsequent to implantation and engagement of the plate prosthesis 100 with the humerus 10. In still other embodiments, the plate body 102 may include a plurality of indicia that indicate or mark one or more of the suture anchor attachment locations 120 for formation of the openings/recesses 122 in situ or intraoperatively subsequent to implantation of the plate body 102. Such indicia may include indents, colors, different materials, or any other suitable indicia for marking one or more of the suture anchor attachment locations 120. In another embodiment, the plate body 102 need not include indicia that indicate or mark the suture anchor attachment locations 120. Instead, the surgeon may select the suture anchor attachment locations 120 freehand for formation of the openings/recesses 122.

In one embodiment, the openings/recesses 122 may extend entirely through a thickness of the plate body 102 from the upper surface 104a to the lower surface 104b. However, in other embodiments, the openings/recesses 122 may extend only partly through a thickness of the plate body 102 from the upper surface 104a toward the lower surface 104b. Additionally, in one embodiment, each of the anchor seats defined by the openings/recesses 122 may be provided with a conically-shaped or angled inner wall similar to the inner wall 34, 134 illustrated and described above with regard to the suture anchor attachment locations 30, 130. However, in other embodiments, the openings/recesses 122 may be provided with a circular cylindrical inner wall similar to the inner wall 234 illustrated and described above with regard to the suture anchor attachment location 230. Additionally, although the suture anchor attachment locations 120 are configured as openings/recesses 122 extending at least partially through various regions of the plate body 102, in other embodiments, the suture anchor attachment locations 120 may be configured as a stem or projection extending outwardly from the upper surface 104a of the plate body 102 similar to the stems/projections 332 illustrated and described above with regard to the suture anchor attachment location 330.

Additionally, as discussed in detail above, the suture anchors 40 are configured for engagement with a select one of the suture anchor attachment locations to selectively attach the suture anchors 40 (and the sutures S) to one or more portions of the plate body 102. As also discussed in detail above, the sutures S may be attached to the suture anchors 40 by any suitable method including, for example, by threading the sutures S through one or more openings/apertures/eyes (not shown) in the anchors 40, via knotting (FIGS. 11-14), a fastener, an adhesive, or other know techniques for attaching sutures to other structures/devices. As should be appreciated, the suture anchors 40 are sized and shaped for positioning within the openings/recesses 122 of the suture anchor attachment locations 120. Additionally, each of the suture anchor attachment locations 120 may be provided with one or more engagement elements configured for mating engagement with a corresponding engagement element defined by the suture anchor 40 to selectively retain/secure the suture anchor 40 in position relative to the suture anchor attachment location 120. As discussed above with regard to the prosthesis 20, such engagements elements may include a projection/tongue/ring/flange positioned within a corresponding recess/groove, mating threads, ratchet/ratcheting elements, snap-in engagement elements, frictional engagement elements, interference-type elements, or other types of engagement elements suitable to selectively engage the suture anchor 40 with the suture anchor attachment location 120. In other embodiments, the suture anchors 40 may be inserted into the opening/recess 122 of the suture anchor attachment location 120 from the underside or lower surface 104b of the plate body 102, with the suture anchor 40 positioned in abutment against an inner shoulder or tapered surface defined within the opening/recess 122 to prevent the suture anchor 40 from passing through the opening/recess 122, thereby engaging the suture anchor 40 to the plate body 102. Additionally, in still other embodiments, the plate body 102 may be provided with suture anchor attachment locations configured for direct engagement with a knotted portion K of the sutures S, as described in detail above with regard to the suture attachment locations 30' and 30".

Having described the elements and features associated with the plate prosthesis 100, reference will now be made to use of the prosthesis 100 to repair one or more fractures of the upper extremity of the humerus 10 according to one form of the present invention. However, it should be understood that the disclosed use is exemplary in nature, and that other uses of the plate prosthesis 100 are also contemplated as falling within the scope of the present invention.

As illustrated in FIG. 15, in a traumatic accident, the humerus 10 may break into several fragments along one or more fracture lines, including separation of the upper extremity of the humerus 10 from the humeral shaft 18 along a fracture line $F_3$ at or near the surgical neck. The plate prosthesis 100 may be used to repair this type of fracture and/or other types of fractures of the humerus 10 or fractures of other bones. In one embodiment, the elongate plate body 102 is positioned across the fracture line $F_3$ with the proximal plate portion 102a positioned adjacent the upper extremity of the humerus 10, and more specifically along a superior aspect of the greater tuberosity 14, and with the distal plate portion 102b positioned along the humeral shaft 18. Additionally, the plate body 102 may be provisionally attached to the humerus 10 via a number of pins or fasteners (not shown) extending through the provisional fixation holes 107.

The proximal plate portion 102a may be securely/terminally attached to the upper extremity of the humerus 10 via insertion of one or more of the bone anchors 110 through corresponding ones of the openings 106 in the proximal plate portion 102a with the threaded shank 112 securely anchored in bone tissue. The distal plate portion 102b may be attached to the humeral shaft 18 via insertion of one the bone anchors 110 through the slotted opening 108 in the distal plate portion 102b with the threaded shank 112 securely anchored in bone tissue. The bone fragments on each side of the fracture line $F_3$ may be displaced toward one another via any suitable displacement technique or reduction to reduce the fracture. During reduction of the fracture, the bone anchor 110 extending through the slotted opening 108 is translated along the length of the slotted opening 108. After reduction of the fracture, one or more additional bone anchors 110 may be used to further terminally secure the proximal and distal plate portions 102a, 102b to the humerus 10, thereby resulting in definitive fixation of the plate body 102 to the humerus 10.

Following anchoring of the plate body 102 to the humerus 10 and reduction of the fracture, the sutures S are attached to select portions of the plate body 102 via engagement of the suture anchors 40 to select ones of the suture anchor attachment locations 120. The location of the sutures S can be optimized to facilitate engagement with the greater and lesser tuberosity fragments 14, 16 and the humeral shaft 18. As should be appreciated, the surgeon can quickly and easily attach the suture anchors 40 to the proper suture anchor attachment locations 120 that will result in optimal placement and organization (i.e., draping) of the sutures S relative to the tuberosity fragments 14, 16 and the humeral shaft 18. In one embodiment, the suture anchors 40 are attached to the suture anchor attachment locations 120 in-situ or intraoperatively subsequent to anchoring of the plate body 102 to the humerus 10. However, in other embodiments, the suture anchors 40 may be pre-attached to the suture anchor attachment locations 120 prior to anchoring of the plate body 102 to the humerus 10. Additionally, in one embodiment, the sutures S may be engaged to corresponding ones of the suture anchors 40 in-situ or intraoperatively subsequent to anchoring of the plate body 102 to the humerus 10. However, in other embodiments, the suture anchors 40 may be pre-engaged or pre-loaded to the suture anchors 40 prior to anchoring of the plate body 102 to the humerus 10. In a further embodiment, a number of plugs or inserts may be provided to cover any unused openings/recesses 122 of the suture anchor attachment locations 120 (i.e., to cover the openings/recesses 122 that are not engaged with one of the suture anchors 40).

As discussed in detail above, in a further aspect of the invention, the sutures S and/or the suture anchors 40 may be provided with anatomy based color-coding. For example, the sutures S and/or the suture anchors 40 can be color coded to correspond to a particular portion of the humerus 10 (i.e., tuberosity fragments 14, 16 and the humeral shaft 18). For example, a first group of sutures $S_1$ of a first color may be provided for use in association with the greater tuberosity fragment 14, a second group of sutures $S_2$ of a second color may be provided for use in association with the lesser tuberosity fragment 16, and a third group of sutures $S_3$ of a third color may be provided for use in association with the humeral shaft 18. In one exemplary embodiment, red sutures $S_1$ may be provided for use in association with the greater tuberosity fragment 14, green sutures $S_2$ may be provided for use in association with the lesser tuberosity fragment 16, and white sutures $S_3$ may be provided for use in association with the humeral shaft 18. However, it should be understood that any number of sutures S may be utilized in association with various portions of the humerus 10, and that other suture colors are also contemplated for use in association with the present invention. Additionally, the colored sutures S need not necessarily define a solid color. For example, in one embodiment, one or more of the suture S may be formed of a plurality of white suture threads/strands interwoven or integrated with a colored (i.e., non-white) tracer thread/strand. It should further be understood that the sutures S may be provided with other types of indicia-coding other than color including, for example, various types of markings or markers associated with specific suture groups.

Following attachment of the suture anchors 40 to select ones of the suture anchor attachment locations 120 and draping of the sutures S (i.e., color-coded suture groups $S_1$, $S_2$ and $S_3$) to properly position and organize the sutures S relative to the plate body 102 and the anatomy of the humerus 10, the sutures S are engaged/tied to the upper and lower tuberosities 14, 16 and the humeral shaft 18 to further anchor/engage the plate body 102 to the humerus 10 and/or to facilitate compression and reduction of bone fragments to their proper anatomic position and orientation. As should be appreciated, the present invention may reduce the overall length and complexity of the surgical procedure to repair humeral fractures (or other types of fractures) compared to conventional surgical repair techniques. As should be further appreciated, the present invention provides the surgeon with the flexibility of selecting locations for attachment of the sutures S from multiple locations on the plate body 102. Additionally, reduction of bone fragments to their proper anatomic position/orientation may also be optimized.

In a further form of the invention, the elements and components of the shoulder prosthesis 20 or the plate prosthesis 100 may be provided as a prosthesis kit. For example, a kit may be provided which includes the components of the shoulder prosthesis 20 (i.e., the stem portion 22, the body portion 24, the head portion 26 and the connector portion 28) in either an assembled or disassembled configuration in combination with a plurality of the suture anchors 40 and the sutures S. Additionally, a kit may be provided which includes the components of the plate prosthesis 100 (i.e., the plate body 102 and a plurality of the bone anchors 110) in combination with a plurality of the suture anchors 40 and the sutures S.

In one embodiment, the prosthesis kit may include suture anchors 40 that are pre-attached to the suture anchor attachment locations 30, 120. In another embodiment, the suture anchors 40 may be detached from the suture anchor attachment locations 30, 120 and placed in separate packaging. In a further embodiment, the sutures S may be pre-loaded or pre-attached to the suture anchors 40 may be detached from the suture anchor attachment locations 30, 120 and placed in separate packaging. However, in another embodiment, the sutures S may be detached from the suture anchors 40 and placed in separate packaging. In a further embodiment, the kit may include a number of plugs or inserts that may be used to cover any unused openings/recesses 32, 122 of the suture anchor attachment locations 30, 120 (i.e., to cover the openings/recesses 32, 122 that are not engaged with one of the suture anchors 40). In a further embodiment, the kit may include components of the prosthesis 20, 100 which define a plurality of the suture anchor attachment locations including pre-formed or pre-drilled openings/recesses 32, 122. However, in another embodiment, the kit may include components of the prosthesis 20, 100 which do not include pre-formed or pre-drilled openings/recesses 32, 122, but instead include a plurality of indicia that indicate or mark one or more of the suture anchor attachment locations for formation of the openings/recesses 32, 122 in situ or intraoperatively subsequent to implantation of the prosthesis 20, 100. Such indicia may include indents, colors, different materials, or any other suitable indicia for marking one or more of the suture anchor attachment locations. In still other embodiments, the prosthesis 20, 100 need not include indicia that indicate or mark the suture anchor attachment locations. Instead, the surgeon may select the suture anchor attachment locations freehand for formation of the openings/recesses 32, 122.

In another embodiment, the prosthesis kit may include one or more sizes and/or varied configurations of the body portion 24 of the shoulder prosthesis 20. For example, the kit may include a plurality of different sizes of the body portion 24 (i.e., small, medium, large, etc.) and/or the kit may include a plurality of body portions 24 having different layouts/arrangements of the suture anchor attachment locations 30 to accommodate various types of bone fractures or treatment techniques. In other embodiments, the prosthesis kit may include one or more sizes and/or configurations of the stem portion 22, the head portion 26 and/or the connector portion 28. Similarly, a prosthesis kit may be provided which includes one or more sizes and/or varied configurations of the plate body 102 of the plate prosthesis 100. For example, the kit may include a plurality of different sizes of the plate body 102 (i.e., small, medium, large, etc.) and/or the kit may include a plurality of the plate bodies 102 having different layouts/arrangements of the suture anchor attachment locations 120 and/or different layouts/configurations of the openings 106, 108 to accommodate various types of bone fractures or treatment techniques. Additionally, in other embodiments, the prosthesis kit may include one or more sizes and/or configurations of the bone anchors 110.

While the present invention described herein has been described for use in association with an orthopedic prosthesis, it should be understood that the present invention may also be used in association with other types of prostheses. In reading the claims, words such as "a", "an", "at least one", and "at least a portion" are not intended to limit the claims to only one item unless specifically stated to the contrary. Additionally, when the language "at least a portion" and/or "a portion" is used, the claims may include a portion and/or the entire item unless specifically stated to the contrary. Furthermore, when the term "distal" is used with respect to a structure, the term refers to the far end of the structure, and when the term "proximal" is used with respect to a structure, the term refers to the near end of the structure.

Various changes and modifications to the described embodiments set forth herein will be apparent to those skilled in the art, and such changes and modifications can be made without departing from the spirit and scope of the invention and without diminishing its intended advantages. Additionally, while the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

What is claimed is:

1. An orthopedic prosthesis, comprising:
    a shoulder prosthesis including a stem portion extending along a longitudinal axis, a head portion, and a body portion extending between said stem portion and said head portion, wherein said shoulder prosthesis includes a plurality of suture anchor attachment locations, each of said suture anchor attachment locations comprising a first engagement element; and
    a plurality of suture anchors, each of said suture anchors including one or more sutures extending from an anchor portion, said anchor portion comprising a second engagement element for engagement with said first engagement element of a select one of said suture anchor attachment locations to selectively attach a corresponding one of said suture anchors to said shoulder prosthesis,
    wherein the body portion includes a pair of arcuate recesses that define a fin extending in a direction parallel to the longitudinal axis and structured to abut a greater tuberosity fragment and a lesser tuberosity fragment of a patient's shoulder for reduction of said greater and lesser tuberosity fragments to a proper anatomic position.

2. The orthopedic prosthesis of claim 1 wherein said suture anchor attachment locations each comprise an opening extending at least partially through a thickness of said shoulder prosthesis; and wherein said anchor portion of said corresponding one of said suture anchors is positionable within said opening and is retainable in said opening by engagement of said first engagement element with said second engagement element.

3. The orthopedic prosthesis of claim 2 wherein said anchor portion includes an outer end wall positioned substantially flush with or recessed below an outer surface of said shoulder prosthesis when said anchor portion is positioned within said opening.

4. The orthopedic prosthesis of claim 2 wherein said anchor portion includes an outer sidewall engageable with a corresponding inner sidewall of said opening.

5. The orthopedic prosthesis of claim 4 wherein each of said outer sidewall of said anchor portion and said inner sidewall of said opening has either a conical shape or a circular cylindrical shape.

6. The orthopedic prosthesis of claim 4 wherein one of said outer sidewall of said anchor portion and said inner sidewall of said opening defines a recess; wherein another of said outer sidewall of said anchor portion and said inner sidewall of said opening defines a projection; and wherein said projection is positionable within said recess to provide said engagement of said first engagement element with said second engagement element.

7. The orthopedic prosthesis of claim 6 wherein said recess comprises an annular groove; and wherein said projection comprises a ring or clip positionable within said annular groove to provide said engagement of said first engagement element with said second engagement element.

8. The orthopedic prosthesis of claim 6 wherein said projection is formed of an elastic material to facilitate positioning of said projection within said recess.

9. The orthopedic prosthesis of claim 4 wherein one of said outer sidewall of said anchor portion and said inner sidewall of said opening defines a first threaded portion; and wherein another of said outer sidewall of said anchor portion and said inner sidewall of said opening defines a second threaded portion configured to threadingly engage with said first threaded portion to provide said engagement of said first engagement element with said second engagement element.

10. The orthopedic prosthesis of claim 1 wherein one of said first and second engagement elements comprises a recess; wherein another of said first and second engagement elements comprises a projection; and wherein said projection is positionable within said recess to provide said engagement of said first engagement element with said second engagement element.

11. The orthopedic prosthesis of claim 10 wherein said recess comprises an annular groove, and wherein said projection comprises a ring or clip positionable within said annular groove to provide said engagement of said first engagement element with said second engagement element.

12. The orthopedic prosthesis of claim 10 wherein said projection is formed of an elastic material to facilitate positioning of said projection within said recess.

13. The orthopedic prosthesis of claim 1 wherein one of said first and second engagement elements comprises a first threaded portion; wherein another of said first and second engagement elements comprises a second threaded portion; and wherein said first threaded portion is configured to threadingly engage with said second threaded portion to provide said engagement of said first engagement element with said second engagement element.

14. The orthopedic prosthesis of claim 1 wherein said first and second engagement elements are configured to engage with one another by a friction fit.

15. The orthopedic prosthesis of claim 1 wherein said suture anchor attachment locations each comprise a stem extending from an outer surface of said shoulder prosthesis; wherein said anchor portion of said corresponding one of said suture anchors comprises an opening; and wherein said stem of said suture anchor attachment location is positionable within said opening in said anchor portion and is retainable in said opening by said engagement of said first engagement element with said second engagement element.

16. The orthopedic prosthesis of claim 1 wherein each of said suture anchors includes a plurality of sutures extending from said anchor portion.

17. The orthopedic prosthesis of claim 1 wherein said plurality of suture anchors includes:
   a first suture anchor including a plurality of sutures having a first color-coding; and
   a second suture anchor including a plurality of sutures having a second color-coding different from said first color-coding.

18. The orthopedic prosthesis of claim 17 wherein said first and second color-codings are anatomy based; and wherein said first color-coding associated with said plurality of sutures of said first suture anchor corresponds to a first bone region; and wherein said second color-coding associated with said plurality of sutures of said second suture anchor corresponds to a second bone region.

19. The orthopedic prosthesis of claim 1 wherein each individual suture anchor of said plurality of suture anchors includes sutures that are provided with a unique color-coding corresponding to a particular bone region or bone fracture.

20. The orthopedic prosthesis of claim 1 wherein said body portion includes at least one of said suture anchor attachment locations.

21. The orthopedic prosthesis of claim 20 wherein said head portion has an underside surface facing said body portion, said underside surface including at least one of said suture anchor attachment locations.

22. The orthopedic prosthesis of claim 1 wherein the anchor portion of at least one of the plurality of suture anchors comprises a rigid body separate from the corresponding one or more sutures of the at least one of the plurality of suture anchors; and
   wherein the rigid body is pre-operatively secured to the corresponding one or more sutures prior to attachment of the anchor portion to the corresponding suture anchor attachment location.

23. The orthopedic prosthesis of claim 1 wherein the body portion includes a plurality of teeth positioned opposite said fin and structured to secure the one or more sutures from movement in at least one direction.

24. The orthopedic prosthesis of claim 23 wherein each tooth of the plurality of teeth extends in a direction generally perpendicular to the longitudinal axis.

* * * * *